United States Patent [19]
Yokoi et al.

[11] Patent Number: 5,749,829
[45] Date of Patent: May 12, 1998

[54] ENDOSCOPE SYSTEM

[75] Inventors: Takeshi Yokoi, Hino; Takahiro Kishi, Machida; Tsutomu Ishiguro, Hachioji; Masaaki Nakazawa, Hino; Yukio Takahashi, Hachioji; Hideo Ito, Akishima; Hisao Yabe, Hachioji; Satoshi Nakagawasai, Tokyo, all of Japan

[73] Assignee: Olympus Optical Co., Ltd., Tokyo, Japan

[21] Appl. No.: 593,341

[22] Filed: Jan. 29, 1996

[30] Foreign Application Priority Data

May 16, 1995 [JP] Japan ..................... 7-117525

[51] Int. Cl.⁶ ................................................ A61B 1/00
[52] U.S. Cl. ............................... 600/153; 600/155
[58] Field of Search ............................ 600/121, 133, 600/153, 154, 155, 156, 157

[56] References Cited

U.S. PATENT DOCUMENTS

| | | | |
|---|---|---|---|
| 4,637,378 | 1/1987 | Sasa. | |
| 4,667,655 | 5/1987 | Ogiu et al. | 600/157 X |
| 5,167,220 | 12/1992 | Brown | 600/157 |
| 5,301,656 | 4/1994 | Negoro et al. | 600/133 X |

*Primary Examiner*—Beverly M. Flanagan
*Attorney, Agent, or Firm*—Armstrong, Westerman, Hattori, Mcleland & Naughton

[57] ABSTRACT

An endoscope system in accordance with the present invention comprises: an endoscope having an insertional part, operation unit, and connector unit set in array, and including channels that communicate with an opening formed in the distal section of the insertional part and an opening formed in the operation unit or connector unit; and at least one cleaning instrument having a flexible tube that can be connected to the opening formed in the operation unit or connector unit of the endoscope and that has the overall length thereof set to 30 cm or larger.

19 Claims, 23 Drawing Sheets

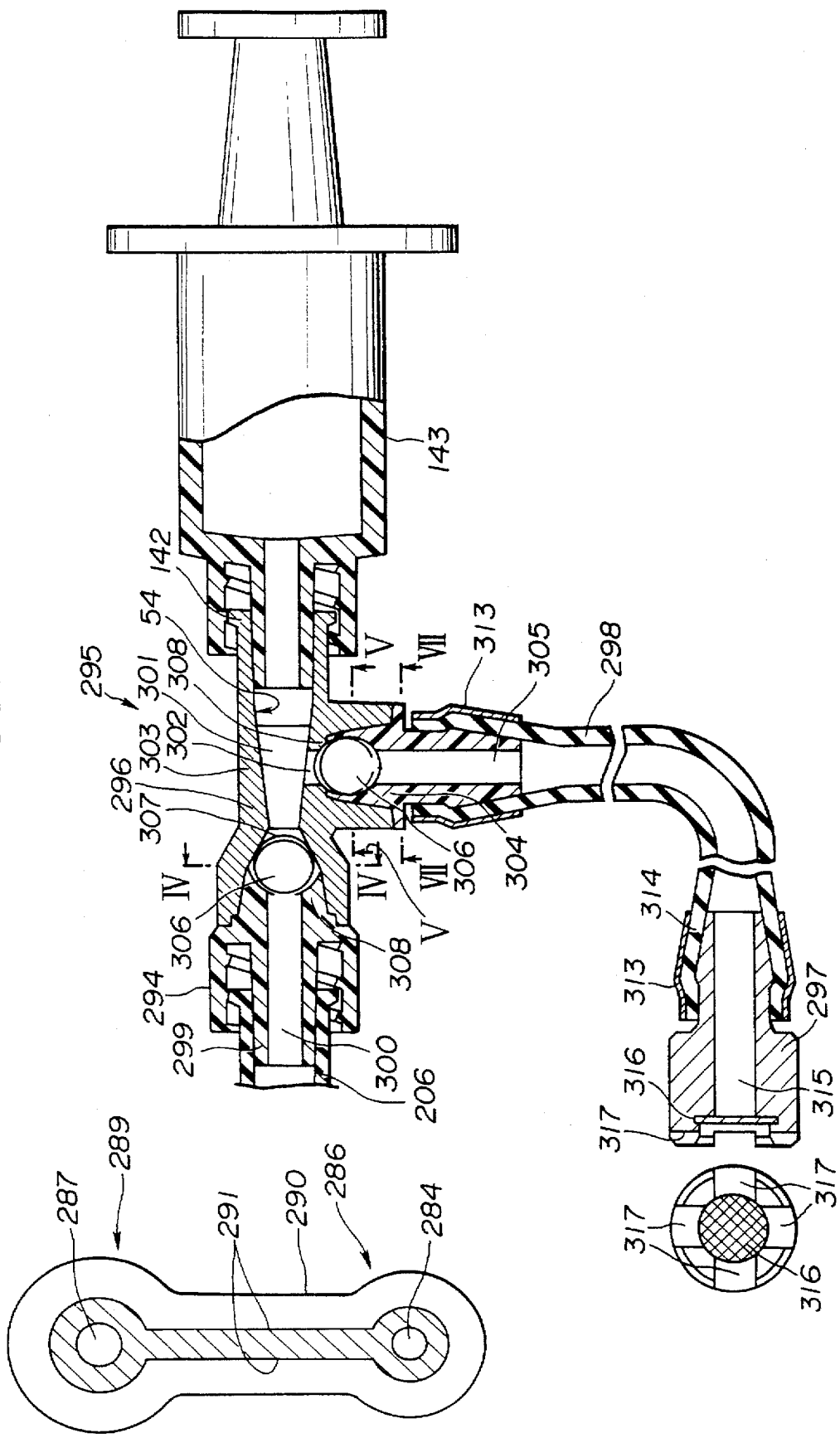

ENDOSCOPE SYSTEM

BACKGROUND OF THE INVENTION

1. Field of the Invention

The present invention relates to an endoscope system having an endoscope for observing or treating a subject and a cleaning instrument for keeping the endoscope clean.

2. Description of the Related Art

In the past, it has been known in an endoscope system that cleaning is performed after every use by supplying a cleaning solution to various kinds of channels that are designed for aeration, perfusion, suction, and the like and that lie through an endoscope. An endoscope channel cleaning device disclosed in Japanese Patent Laid-Open No. 3-8213 is a known instrument for cleaning channels in an endoscope. The disclosed endoscope channel cleaning device has a structure in which two short tubes and a long tube joined with one another using a branch tube shaped like a letter Y. Another structure in which the overall length of one of the short tubes is made longer and the terminal of the tube is connected to an aeration base has also been disclosed. In either of the structures, a Y-shaped branch tube is used to bifurcate a single channel into two channels.

For supplying a liquid, a syringe is attached to an end of one long tube. Either an aeration/perfusion syringe and suction syringe or both a suction syringe and aeration base are attached to the other end thereof, whereby a liquid is fed simultaneously for cleaning.

However, the endoscope channel cleaning device disclosed in the Japanese Patent Laid-Open No. 3-8213 is of a type in which a liquid is injected into two positions simultaneously through one inlet. Although an injection balance is kept by means of an orifice or similar, since the inner diameters of channels vary greatly in the range from 2 mm to 6 mm, it is difficult to inject a liquid through one inlet into two channels having different inner diameters simultaneously in a well-balanced manner without any loss. The syringe manipulation frequency increases by the number of losses. Consequently, a worker must incur a larger burden, and it takes much time to complete cleaning.

For cleaning an endoscope, the endoscope is placed on a sink or in or by a cleaning vessel on a work desk. At this time, depending on the length of a flexible tube of a cleaning instrument, a cleaning worker is obliged to assume an unnatural posture that is a state in which he/she is lifting an endoscope for a prolonged period of time or stooping for a prolonged period of time.

If the flexible tube of the cleaning instrument is too long, the total amount of liquid increases by the amount of liquid filling the tube. The liquid cannot therefore be injected into channels with a single manipulation of a syringe. The syringe must therefore be manipulated repeatedly. Thus, not only the manipulation frequency increases but also liquid injection and drainage become necessary.

OBJECTS AND SUMMARY OF THE INVENTION

An object of the present invention is to provide an endoscope system in which when cleaning an endoscope, a worker can work on the endoscope in a posture not burdening him/her.

Another object of the present invention is to provide an endoscope system permitting excellent cleaning workability by reducing the frequency of injecting a cleaning solution using a cleaning instrument.

Briefly, an endoscope system of the present invention comprises an endoscope having an insertional part, operation unit, and connector unit set in array, and including channels communicating with an opening formed in the distal portion of the insertional part and with an opening formed in the operation unit or connector unit, and at least one cleaning instrument having a flexible tube that can be connected to the opening formed in the operation unit or connector unit of the endoscope and has an overall length thereof set to 30 cm or larger.

BRIEF DESCRIPTION OF THE DRAWINGS

FIG. 1 is an side view showing the configuration of an endoscope;

FIG. 2 shows the operation exerted when cleaning water is injected to a distal aeration channel and distal perfusion channel using an aeration/perfusion channel cleaning adaptor;

FIG. 3 shows the operation exerted when cleaning water is injected through a connector-side aeration channel and connector-side perfusion channel;

FIG. 4 shows the operation exerted when a suction tube of a suction unit is used to automatically drain liquids remaining in the aeration and perfusion channels;

FIG. 5 shows the operation exerted when a mounting rubber of a suction cleaning adaptor is mounted in a forceps inlet and a suction tube of a suction unit is coupled to a suction base in order to clean all suction-related channels;

FIG. 24 is an IV—IV sectional view of FIG. 16;

FIG. 25 is a sectional view showing a major portion of an injection adaptor;

DETAILED DESCRIPTION OF THE PREFERRED EMBODIMENT

Figure 1:
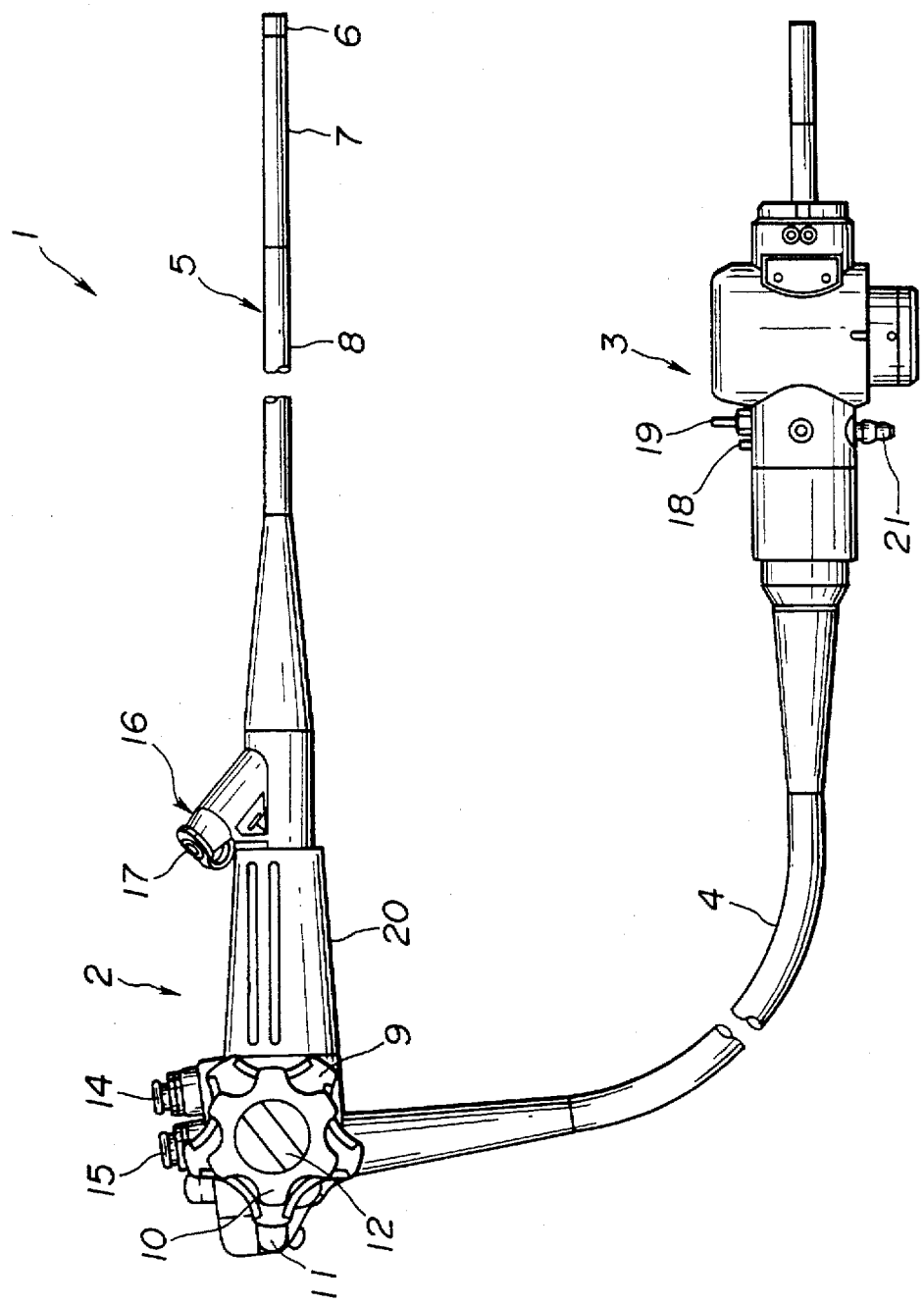
FIGS. 1 to 5 relate to an embodiment of the present invention.

Referring to the drawings, embodiments of the present invention will be described below.

Referring to FIGS. 1 to 5, an embodiment of the present invention will be described.

As shown in FIG. 1, an endoscope 1 has a universal cord 4 linking an operation unit 2 and connector unit 3 and being realized with a flexible tube, and an insertional part 5 that extends from the operation unit 2, is inserted, for example, to a body cavity, and has an elongated shape and flexibility.

The insertional part 5 has a distal section 6, bending section 7, and soft section 8, set in array, in that order, from the distal end thereof. Formed in the vicinity of a grip section 20 of the operation unit 2 located at the back end of the insertional part 5 are an up/down or UD angling knob 9 used for vertical (UD) angling of the bending section 7, an right/left or RL angling knob 10 used for lateral (RL) angling thereof, an UD angle releasing knob 11 for releasing vertical angling, and an RL angle releasing knob 12 for releasing lateral angling.

On the grip section 20, an aeration/perfusion button 14 for use in performing aeration or perfusion via a channel system, which will be described later, running through the endoscope is mounted in an aeration/perfusion cylinder that will be described later, and a suction button 15 used for suction is mounted in a suction cylinder that will be described later.

On the side of the insertional part of the grip section 20, a forceps inlet 16 is formed. A semi-disposable forceps plug 17 is mounted in the forceps inlet 16. Reference numeral 18 written in the connector unit 3 denotes a pressurization base. 19 denotes an aeration base. 21 denotes a suction base.

To begin with, injection of cleaning water or the like into a distal aeration channel and distal perfusion channel using an aeration/perfusion channel cleaning adaptor will be described.

Figure 2:
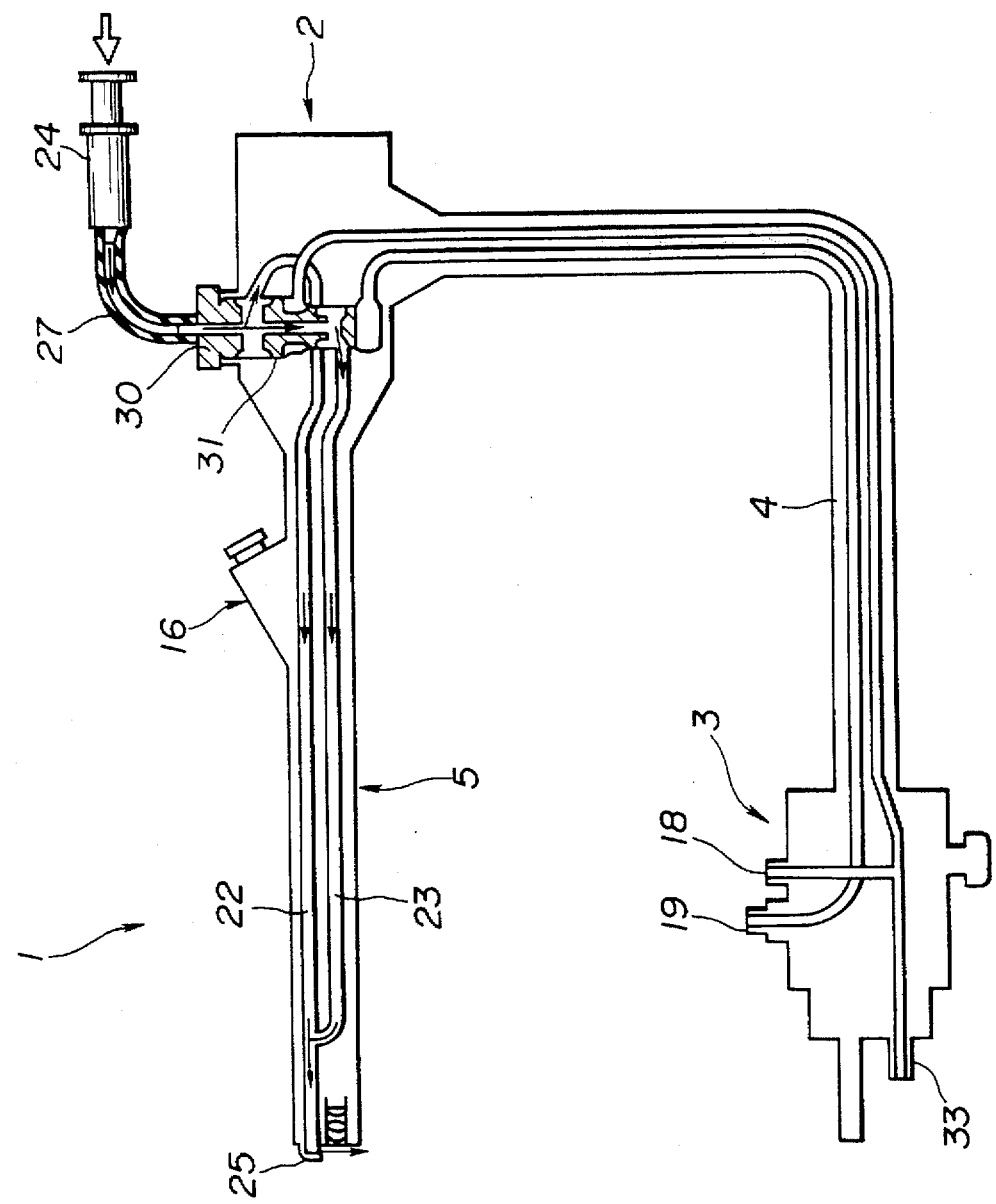

As shown in FIG. 2, assuming that dirt is washed away from the inside of an aeration channel 22 serving as a distal aeration channel and lying through the insertional part 5 of the endoscope 1, the inside of a perfusion channel 23 serving as a distal perfusion channel, and the inside of an aeration/perfusion nozzle 25, first, an aeration/perfusion channel cleaning adaptor 30 is attached to an aeration/perfusion cylinder 31 in the operation unit 2 of the endoscope 1. A syringe 24 serving as a cleaning instrument is connected to the aeration/perfusion channel cleaning adaptor 30 via a flexible tube 27. A liquid, for example, a cleaning solution, disinfectant solution, rinsing water with which the syringe 24 is filled is injected to the aeration channel 22, perfusion channel 23, and aeration/perfusion nozzle 25 for the purpose of cleaning.

Next, injection of cleaning water or similar into a connector-side aeration channel and connector-side perfusion channel will be described.

Figure 3:
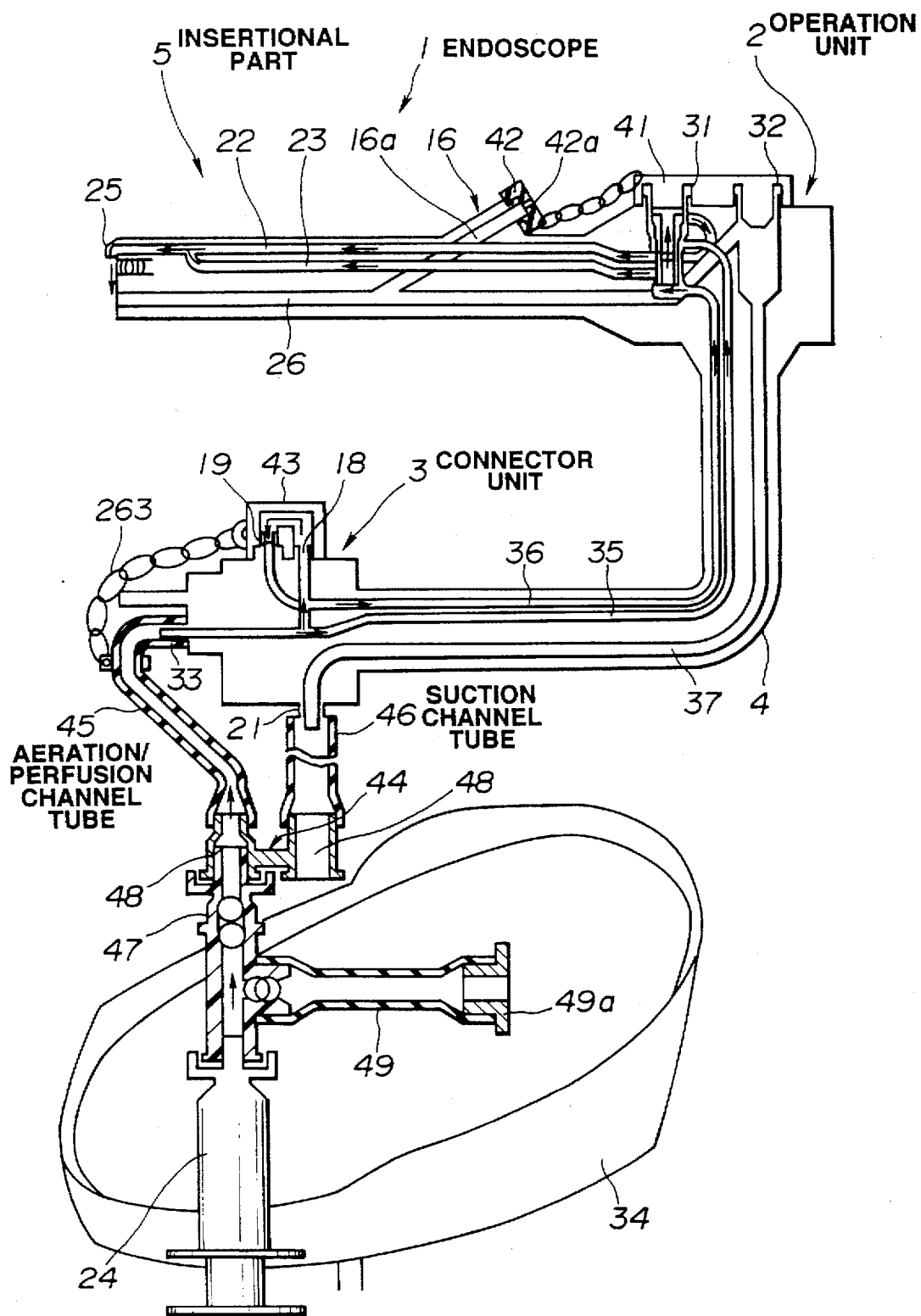

As shown in FIG. 3, assuming that a liquid, for example, a cleaning solution, disinfectant solution, or rinsing water is injected into the aeration channel 22 and perfusion channel 23 by way of an aeration tube 35 serving as a connector-side aeration channel, a perfusion tube 36 serving as a connector-side perfusion channel, and the aeration/perfusion cylinder 31, an all-channel cleaning adaptor 41 is attached to the aeration/perfusion cylinder 31 and a suction cylinder 32 loosely to such an extent that the liquid slightly leaks out. A plug 42 having a leakage hole 42a is then mounted in the forceps inlet 16. A coupling plug 43 is attached to the pressurization base 8 and perfusion base 19 of the connector unit 3.

In this state, an aeration/perfusion channel tube 45 included in an injection tube assembly 44 is press-fitted onto the aeration base 33 of the connector unit 3, and a suction channel tube 46 is press-fitted onto the suction base 21 of the connector unit 3. An injection adaptor 47 is mounted in a tapered section 48 of the injection tube assembly on the side of the aeration/perfusion channel tube 45. In this situation, when a liquid such as a cleaning solution, disinfectant solution, or rinsing water preserved in a vat 34 is injected to the aeration tube 35 and perfusion tube 36 using a syringe 24 whose capacity ranges from 30 cc to 50 cc, the cleaning solution or similar flows into the aeration channel 22 and perfusion channel 23 by way of the aeration/perfusion cylinder 31 and then flows out through the aeration/perfusion nozzle 25.

At this time, a distal portion 49a of a filter unit 49 of the injection adaptor 47 projects outwardly from the liquid in the vat 34 into the air, and the syringe 24 is manipulated for injection. Air is then fed into the channels, whereby the liquids remaining in the channels can be drained off.

When the injection adaptor 47 is mounted in the other tapered section 48 of the injection tube assembly 44 on the side of the suction channel tube 46, if the liquid in the syringe 24 is injected into the suction tube 37 in the same manner as it is injected to the aeration tube 35 and perfusion tube 36, the liquid in the vat can be injected to the suction tube 37, suction cylinder 32, suction channel 26, and forceps passage 16a lying through the forceps inlet 16. When the filter unit 49 projected outwardly from the liquid into the air, if the syringe 24 is manipulated for injection, air can be fed into the channels for easy drainage.

Next, automatic drainage of liquids remaining in aeration and perfusion channels using a suction tube of a suction unit will be described.

Figure 4:
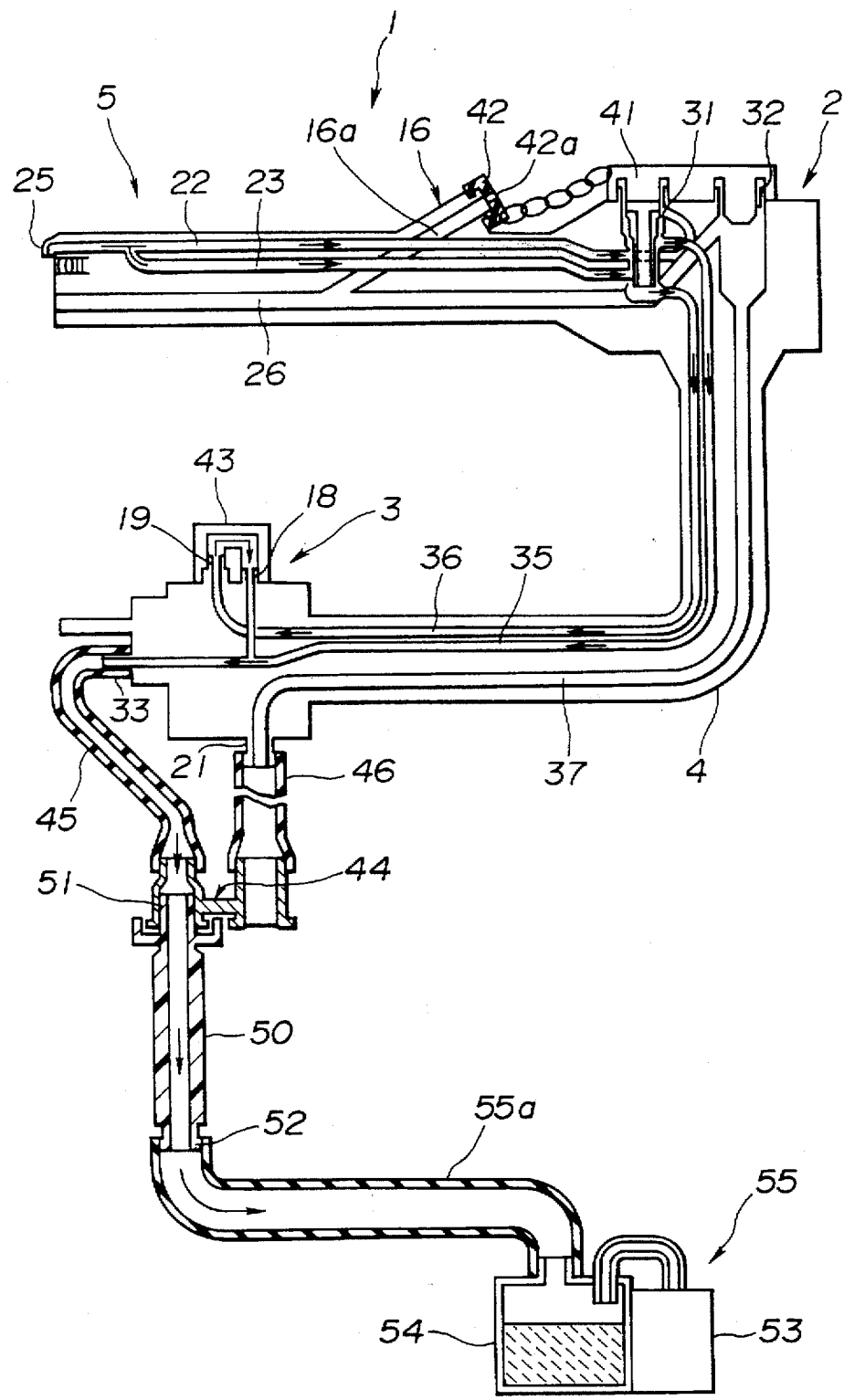

As shown in FIG. 4, a syringe tapered section 51 of a drainage adaptor 50 is mounted in the injection tube assembly 44 in place of the injection adaptor 47. In addition, a suction tube 55a of a suction unit 55 composed of a suction pump 53 and suction tank 54 is connected to a tube connecting section 52 of the drainage adaptor 50. A switch on the suction unit 55 is then turned on in order to supply air, whereby liquids remaining in the aeration and perfusion channels can be drained off automatically. When the drainage adaptor 50 is mounted in the suction-channel side of the injection tube assembly 44, a liquid remaining in the suction channel can be drained off automatically.

Compared with the drainage using the syringe 24 shown in FIG. 3, the automatic drainage by means of the drainage adaptor 50 permits a smaller amount of liquid to remain because of a longer suction period. The automatic drainage is therefore suitable for a pre-process of chamber gas sterilization using ethylene oxide gas, formalin gas, or similar. Moreover, since a remaining liquid can be drained upstream through a nozzle, it can be prevented that the nozzle is clogged or water scales adhere to lenses.

Next, cleaning of all suction channels with a mounting rubber of a suction cleaning adaptor mounted in a forceps inlet and the suction tube of a suction unit connected to a suction base will be described.

Figure 5:
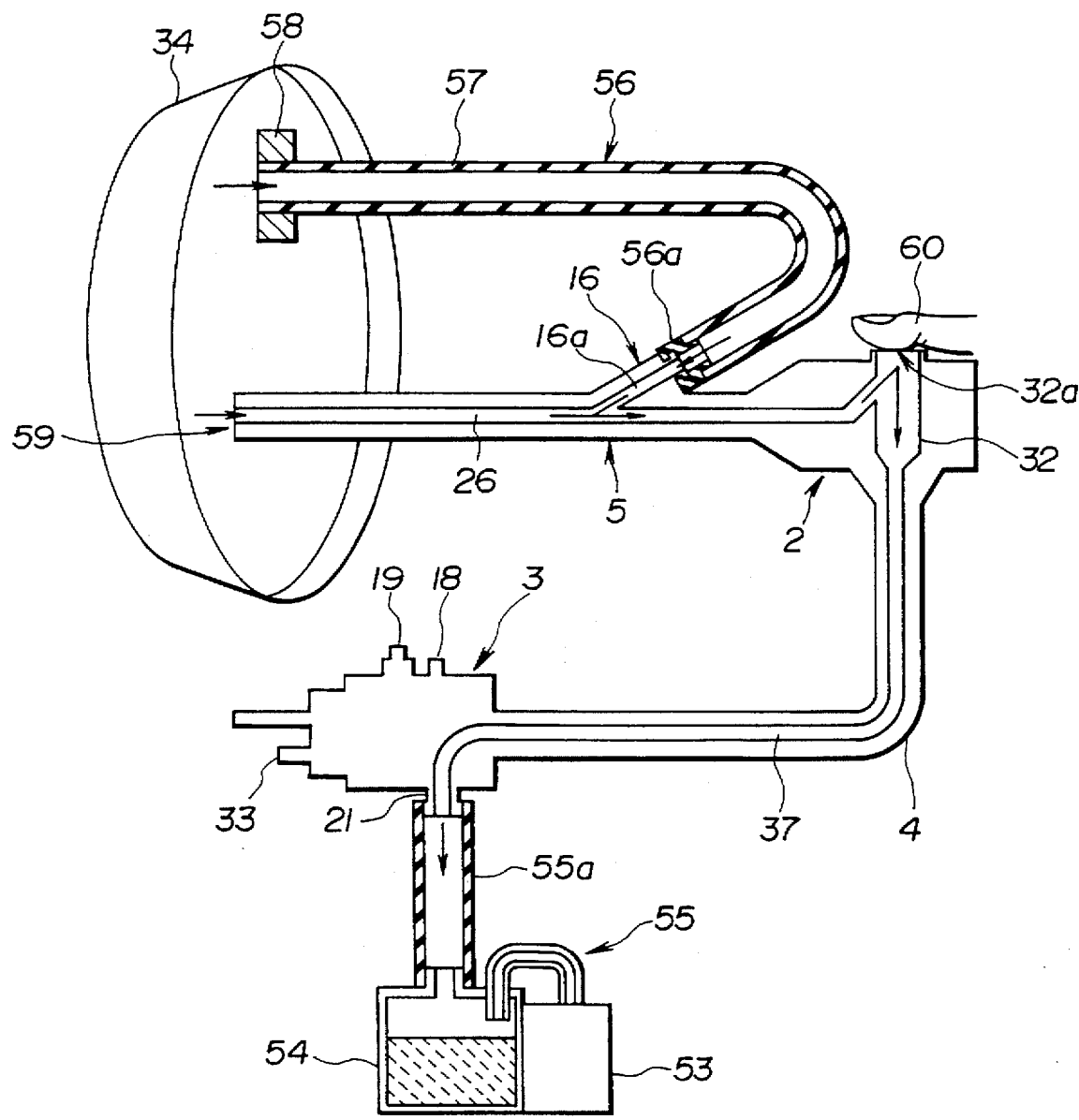

As shown in FIG. 5, a mounting rubber 56a attached to one end of a tube 56 constituting a suction cleaning adaptor 57 is mounted in the forceps inlet 16. In addition, the other end of the tube 56 having a weight 58 such as a ring made of stainless steel, and a suction port 59 formed in the distal section 6 of the insertional part 5 are immersed in a cleaning solution or rinsing water preserved in the vat 34.

The suction tube 55a of the suction unit 55 is connected to the suction base 21 of the connector 3.

An opening 32a of the suction cylinder 32 is blocked by a finger 60, and the switch on the suction unit 55 is turned on. This causes the cleaning solution or rinsing water in the vat 34 to flow into the forceps passage 16a, suction channel 26, and suction tube 37. Thus, all the suction channels are cleaned or rinsed.

At this time, since the weight 58 is attached to the end of the tube 56 constituting the suction cleaning adaptor 57, the end of the suction cleaning adaptor 57 can be reliably immersed in a liquid in the vat 34. When the length of the tube of the suction cleaning adaptor 57 is set to a length permitting easy immersion in the vat 34, the cleaning and rinsing workability improves.

In other words, when cleaning, disinfection, rinsing, and drainage are carried out by connecting a flexible tube to an opening of an insertional part or connector unit of an endoscope and placing the endoscope in a sink or in or by a cleaning vessel, if the tube is too short, freedom is lost to deteriorate workability. By contrast, if the length of the tube is, for example, larger than or equal to 1 m, the tube interferes with handling because it is too long. Moreover, the overall content volume increases by the content volume of the tube. Therefore, liquid supply by means of a syringe becomes insufficient. This poses a drawback that the injection frequency increases.

It has been discussed what the length of a flexible tube included in a cleaning instrument should be in order to lighten the burden a worker must incur during cleaning of an endoscope and to prevent an excessive load from being imposed on the endoscope. The results are listed in Table 1.

TABLE 1

| Item | Result |
| --- | --- |
| Height of a general work desk from the floor (a) | 70 cm |
| Height of a sink or cleaning vessel from the floor (b) | 60 cm |
| Height permitting excellent workability | |
| For a worker 160 cm tall (h1) | 95 cm |
| For a worker 180 cm tall (h2) | 115 cm |
| Length of a tube from an opening when a work desk is used | |
| For a worker 160 cm tall (h1 − a + a) | 30 cm (a = 5 cm) |
| For a worker 180 cm tall (h2 − a + a) | 50 cm (a = 5 cm) |
| Length of a tube from an opening when a sink or cleaning vessel is used | |
| For a worker 160 cm tall (h1 − b + a) | 40 cm (a = 5 cm) |
| For a worker 180 cm tall (h2 − b + a) | 60 cm (a = 5 cm) |

Incidentally, the capacity of a syringe generally used for cleaning of an endoscope ranges from 30 ml to 50 ml. From this viewpoint, the inner diameter of a flexible tube is set to a minimum necessary limit so that the single manipulation of the syringe for injection can cause a cleaning solution or similar to flow into the overall lengths of channels in an endoscope.

In other words, the relationship below is set up among the capacity of a syringe, the capacity of a tube included in the syringe, and the capacity of a formed channel such as the aeration tube 35 or perfusion tube 36.

Tube capacity+Channel capacity<Syringe capacity

Referring to the results listed in Table 1 with this relationship taken into account, it is apparent that when the length of a flexible tube of a cleaning instrument is set to a minimum of 30 cm, or preferably, to 60 cm, a cleaning worker need not assume such a posture that he/she keeps stretching his/her arm while lifting an endoscope or keeps stooping for a prolonged period of time.

When a cleaning instrument is connected to an opening of a connector installed at an end of a universal cord of an endoscope or when a multi-branch tube branching out in a plurality of different directions from the same end is connected, if the bending length of a tube, α, is 5 cm as listed in Table 1, it is insufficient. The discussion has revealed that approximately 15 cm is needed for the bending length α. Consequently, an appropriate length of a tube ranges from 40 cm to 70 cm due to the increase of 10 cm in the α value from 5 cm to 15 cm.

As a result of the foregoing discussion, the length of a flexible tube is in the range from 30 cm or larger to 70 cm or smaller. For example, when the length of a tube is smaller than 20 cm, the tube is too short. A worker must therefore stoop for cleaning. An excessive load is imposed on the worker's lumbar vertebrae. This causes the worker to feel fatigued. By contrast, when the length of a tube is larger than or equal to 80 cm, an excess injection and drainage of a liquid into and from the flexible tube become necessary. The syringe manipulation frequency increases, and the tube becomes a hindrance.

As mentioned above, after endoscopic examination is completed, when an endoscope is placed in a sink or cleaning vessel in order to perform cleaning, disinfection, rinsing, drainage, and the like, since the dimension of a tube is set to the range from 30 cm or larger to 70 cm or smaller, a worker need not assume such a posture that he/she keeps stretching his/her arm while lifting an endoscope or keeps stooping but can achieve cleaning in a natural standing posture.

Since the length of a tube is set properly, the capacity of the tube is set properly. A liquid will therefore not be injected excessively from a syringe into the tube. Since work can be completed by feeding a liquid to all channels with one manipulation for injection, a work loss can be eliminated.

Furthermore, since an end of a tube of a suction cleaning adaptor or injection adaptor is made of a metal in order to exert the effect of a weight, when cleaning or similar is performed, it become unnecessary to support the tube end by a hand and immerse it in a liquid. The workability therefore improves drastically.

Ends of an injection tube assembly have the same shapes as the mounting ports of a syringe or injection adaptor and a drainage adaptor and lie adjacently, so that the ends thereof can be attached airtightly. The syringe or injection adaptor and drainage adaptor can be switched over readily.

For cleaning an endoscope, the whole procedure of cleaning, disinfection, rinsing, and drainage need not always be carried out. A user can select any of the processes in terms of dirt level of an endoscope and of workability. As shown in FIG. 3, the coupling plug 43 and injection tube assembly 44 may be joined with each other by a chain 263 having a length permitting a play for comfortable work. Alternatively, as shown in FIG. 4, the cleaning instrument may not have an injection tube assembly joined with a coupling plug but may have them independent of each other. Furthermore, in this embodiment, the injection tube assembly 44 and injection adaptor 47 are formed mutually separately. Alternatively, the injection tube assembly 44 and injection adaptor 47 may be formed as a united body. Likewise, the drainage adaptor 50 and injection tube assembly 44 may be formed as a united body. Moreover, the all-channel cleaning adaptor 41 and injection tube assembly 44 may be joined with each other by a long chain or string.

The structures of cleaning instruments will be described one by one.

To begin with, the aeration/perfusion channel cleaning adaptor 30 installed in the operation unit 2 will be described with reference to FIGS. 6 to 12.

The aeration/perfusion channel cleaning adaptor 30 is structured to be detachable from the aeration/perfusion cylinder 31 in the grip section 20 of the endoscope 1. The aeration/perfusion cylinder 31 is a cylinder having a substantially cylindrical shape and being mounted in an opening formed in a body 101 of the grip section 20 of the endoscope 1. The aeration/perfusion cylinder 31 is locked in the body 101 with a nut 102 and washer 103 by tightening the nut 102.

An O ring 104 is interposed between the nut 102 and body 101 in order to ensure watertightness. A bottom cover 105 is fixed to the bottom of the aeration/perfusion cylinder 31 by soldering. A distal aeration pipe 110, connector-side aeration pipe 111, distal perfusion pipe 112, and connector-side perfusion pipe 113, which are metallic, are fixed to the lateral circumferential side of the aeration/perfusion cylinder 31 in that order from top to bottom by means of soldering.

A distal aeration channel 114 is connected to a distal aeration pipe 110, and communicates with the aeration/perfusion nozzle 25 formed in the distal section 6 of the insertional part shown in FIG. 2. A connector-side aeration channel 115 is connected to a connector-side aeration pipe 111. The connector-side aeration channel 115 communicates with the metallic aeration base 33 that has an opening in the connector unit 3 and is connected to an aeration pump in a light source unit that is not shown. The connector-side aeration channel 115 branches out inside the connector unit 3 and communicates with the metallic pressurization base 18 having an opening in the connector unit 3.

A distal perfusion channel 116 is connected to a distal perfusion pipe 112 in the same manner as the distal aeration channel 114 is connected to the distal aeration pipe 110, merges into the distal aeration channel 114 inside the insertional part of the endoscope 1, and communicates with the aeration/perfusion nozzle 25 formed in the distal section 6.

A connector-side perfusion channel 117 is connected to the connector-side perfusion pipe 113 in the same manner as the connector-side aeration channel 115 is connected to the connector-side aeration pipe 111, and communicates with the metallic perfusion base 19 having an opening in the connector unit 3.

A piston 106 inserted in the aeration/perfusion cylinder 31 is made of a metal. The piston 106 has flanges 107, 108, and 109. When the piston 106 is inserted in the aeration/perfusion cylinder 31, the flanges 107, 108, and 109 fill the role of a guide. After the piston 106 is inserted in the aeration/perfusion cylinder 31, the flanges 107 and 108 engage with the aeration/perfusion cylinder 31 so as to restrict the radial position of the piston 106.

The piston 106 has four packings 119, 120, 121, and 122, which are made of silicon rubber, formed as united parts thereof. The packings 119, 120, 121, and 122 ensure the watertightness between an upper opening 118 and an opening of the distal aeration channel 114, the one between the opening of the distal aeration channel 114 and an opening of the connector-side aeration channel 115, the one between the opening of the connector-side aeration channel 115 and an opening of the distal perfusion channel 116, and the one between the opening of the distal perfusion channel 116 and an opening of the connector-side perfusion channel 117 respectively in the aeration/perfusion cylinder 31. Since the packings 119, 120, 121, and 122 are thus formed as united parts of the piston 106, there are no clearances between the piston and the packings 119, 120, 121, and 122 respectively. Dirt or similar will therefore not accumulate. When the piston 106 is inserted in the aeration/perfusion cylinder 31, the flanges 107, 108, and 109 fill the role of a guide for not damaging the packings 119, 120, 121, and 122.

After the piston 106 is inserted in the aeration/perfusion cylinder 31, the flange 107 of the piston 106 engages with the aeration/perfusion cylinder 31 between the packing 119 and the opening of the distal aeration channel 114, and the flange 108 thereof engages with the aeration/perfusion cylinder 31 between the packing 120 and the opening of the connector-side channel 115.

In the state in which the piston 106 has been inserted in the aeration/perfusion cylinder 31, the dimensions of the outer circumferences of the piston 106 opposed to the openings of the distal aeration channel 114 and distal perfusion channel 116 are smaller by approximately 1 mm to 3 mm than the inner diameter of the aeration/perfusion cylinder 31. Thus, clearances are preserved between the outer circumferences of the piston 106 and the inner circumference of the aeration/perfusion cylinder 31.

In the state in which the piston 106 has been inserted in the aeration/perfusion cylinder 31, the dimension of the outer circumference of the piston on which the packing 122 is molded is smaller by approximately 2 mm than the outer dimension of the flange 109. The packing 122 can therefore deform easily.

The aeration/perfusion cylinder 31 has a tapered section 124 interposed between the opening of the connector-side aeration channel 115 and the opening of the distal perfusion channel 116. A tapered section 125 of the piston 106 abuts on the tapered section 124, thus restricting the axial position of the aeration/perfusion channel cleaning adaptor 30.

A metallic grip 127 is tightened and fixed to a head 126 of the piston 106. The outer surface of the grip 127 is coated unitedly with a rubber cover 128 made of silicon rubber.

Figure 7:
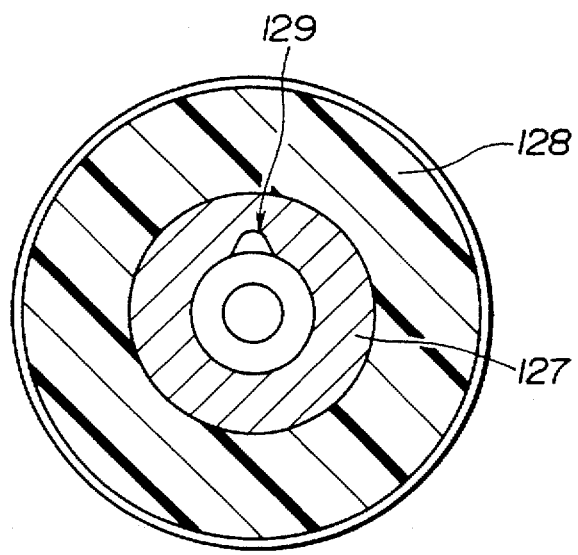
FIG. 7 is an I—I sectional view of FIG. 6.
Figure 8:
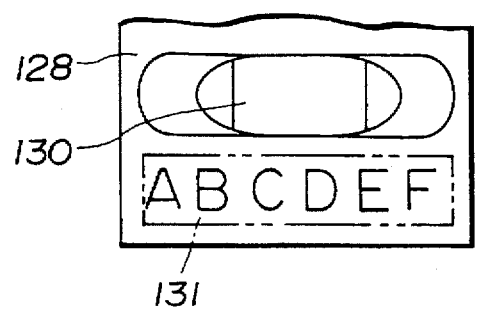
FIG. 8 a view in a direction of an arrow B in FIG. 6.

As shown in FIG. 7, a notch 129 is formed along an inner circumference of the grip 127. When the opening of at least one elongated drainage hole 130 shown in FIG. 8 is molded so that the lateral circumference of the opening can be covered with silicon rubber, the opening acts as a positioner having an indicator 131 in which a model name or similar can be inscribed by molding.

The drainage hole 130 facilitates the efficiency of draining a cleaning solution during cleaning of the aeration/perfusion cleaning adaptor 30. Since molding is performed so that the lateral circumference of the opening of the drainage hole 130 can be covered with silicon rubber, an operator can be protected from being injured.

Figure 6:
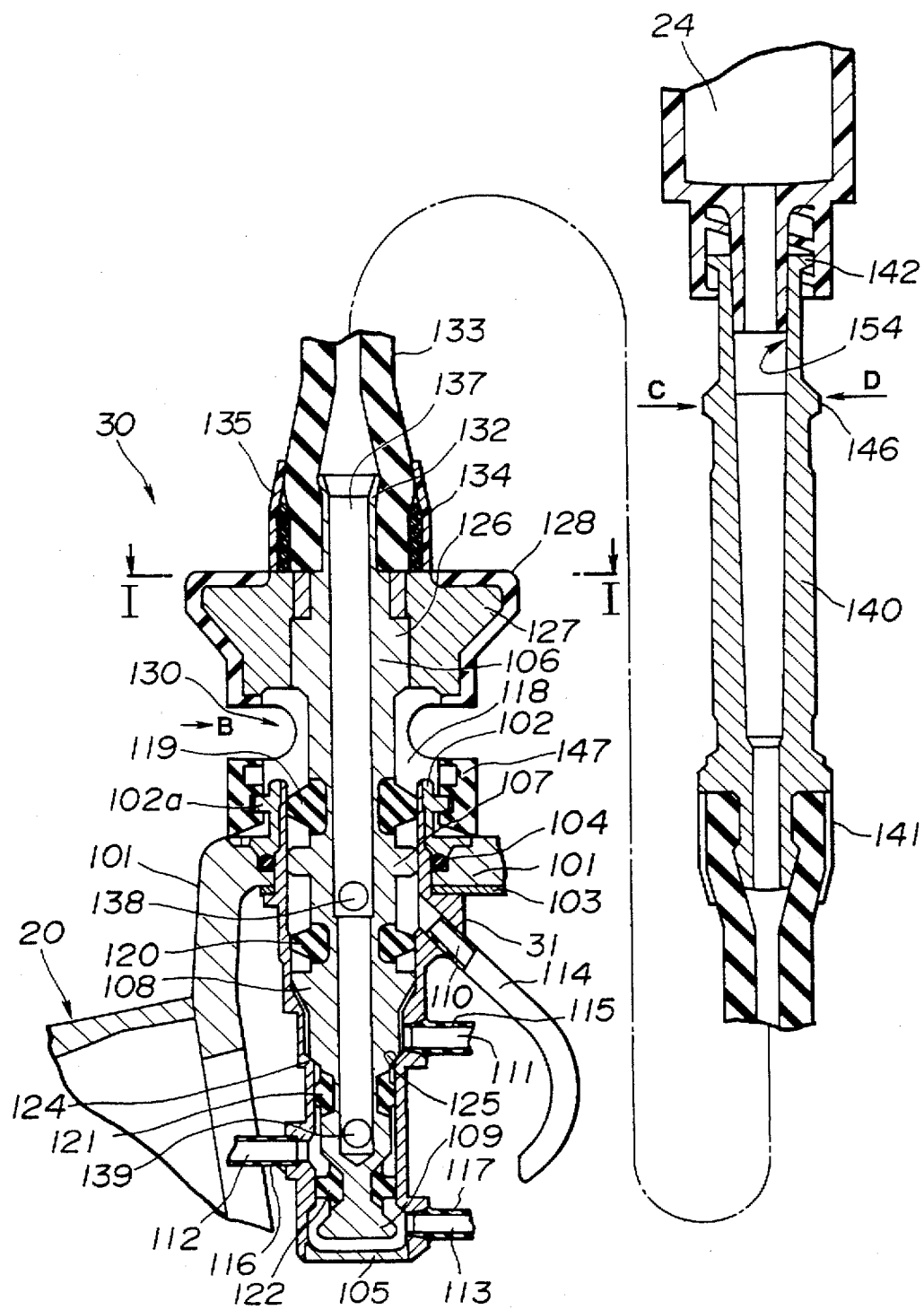
FIG. 6 is a sectional view showing the structure of an aeration/perfusion channel cleaning adaptor.

As shown in FIG. 6, a mounting section 147 is formed below the drainage hole 130 and fixed to a flange 102 of the nut 102 so that the mounting section 147 can be detached and deformed elastically.

When the grip 127 is tightened and fixed to the head 126 of the piston 106, a space created by the notch 129 is filled with an adhesive or similar.

A projection 132 having an inversely-tapered section whose outer diameter gets larger toward the end thereof is formed on the top of the head 126 of the piston 106. A flexible tube 133 made of silicon rubber is attached to the projection 132 using an adhesive. The tube 133 is press-fitted onto the inversely-tapered section of the projection 132, and abutted on the top of the grip 127. The outer circumference of the tube 133 is then pressed and immobilized by a close-winding metallic coil 134. Thereafter, a heat-contractive tube 135 is contracted in order to firmly fix the tube 133 to the projection 132.

The inner diameter of the tube 133 is smaller than the outer diameter of the projection 132. Since the inversely-tapered section of the projection 132 acts as a stopper for preventing the tube 133 from coming off, the tube 133 will not float but is fixed closely. The tube 133 covers the notch 129 of the grip 127.

A communication vertical hole 137 extending from the end of the projection 132 to the vicinity of the packing 122 is bored in the center of the piston 106. Through holes serving as communication transverse holes 138 and 139 whose diameters are smaller than the one of the communication vertical hole 137 are bored in the piston 106 in the vicinities of the openings of the distal aeration channel 114 and distal perfusion channel 116 formed in the aeration/perfusion cylinder 31. This causes the tube 133 to communicate with the distal aeration channel 114 and distal perfusion channel 116.

Figure 12:
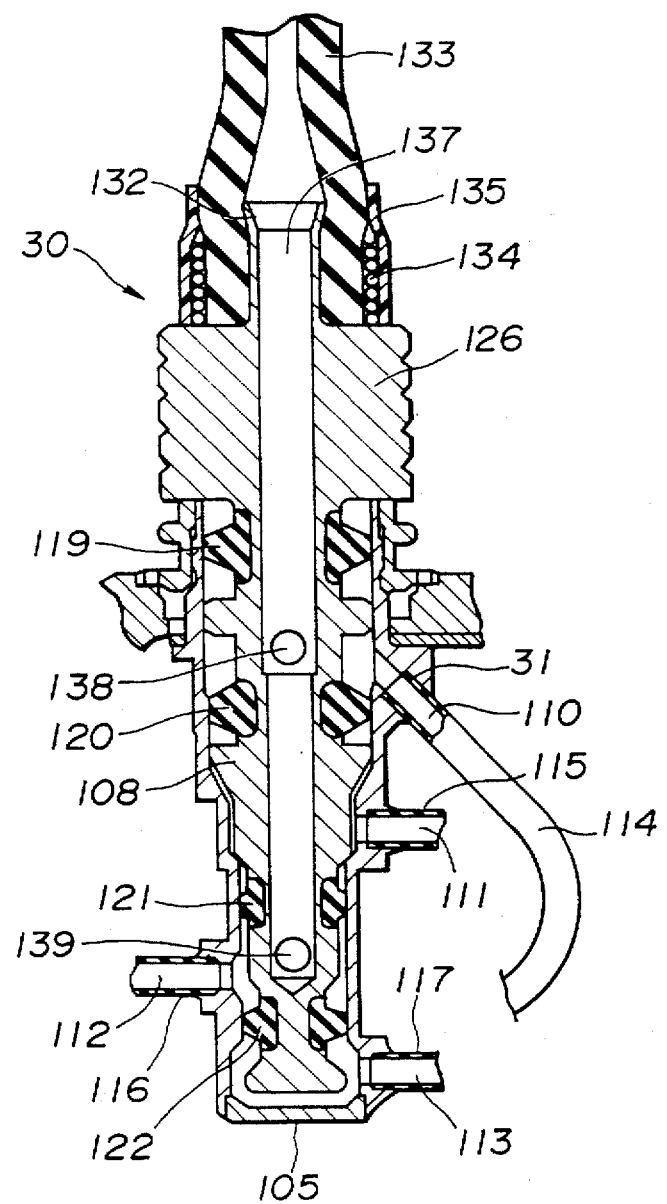
FIG. 12 is a sectional view for explaining another structure of an aeration/perfusion channel cleaning adaptor.

The piston 106 may be structured as shown in FIG. 12, wherein the head 126 serves as a grip. In this case, the components other than the piston 106 are identical to those shown in FIG. 6. The same members as those in FIG. 6 are assigned the same reference numerals, and the description of the members will be omitted.

The other end of the tube 133 is temporarily fixed to a base member 140 made of a rigid resin such as polysulfone (hereinafter PSU). The fixing section is covered with a heat-contractive tube 141 for reinforcement. The length of the tube 133 is set to a length permitting easy manipulation of the syringe 24 during cleaning of an endoscope.

Figure 9:
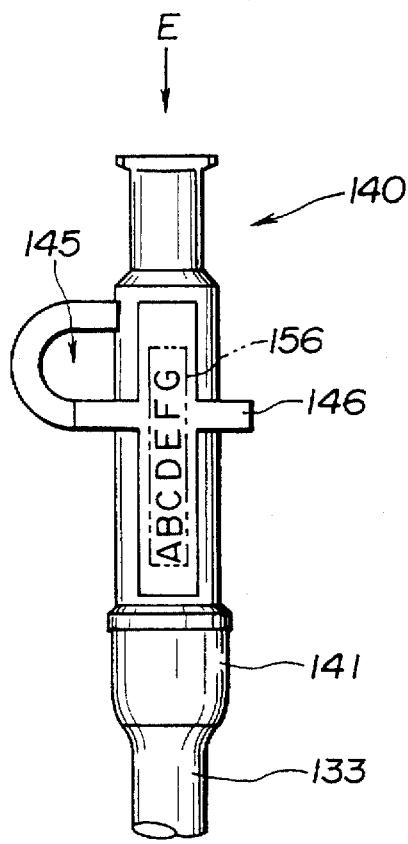
FIG. 9 is a view in a direction of an arrow C in FIG. 6.

As shown in FIGS. 6 and 9, a lure pawl 142 and syringe tapered section 154 are formed in the other end portion of the base member 140. The syringe 24 is connected to the syringe tapered section 154, whereby a liquid such as a cleaning solution can be fed to the distal aeration channel 114 and distal perfusion channel 116. At this time, the syringe 24 can be manipulated with a finger resting on a flange-type finger rest 146 formed on the base member 140. This results in improved manipulability.

When a liquid such as a cleaning solution is injected to the distal aeration channel 114 and distal perfusion channel 116 alone but not fed to the connector-side aeration channel 115 and connector-side perfusion channel 117, a flow velocity and flow rate in feeding a liquid increase. This leads to the improved cleaning efficiency of the aeration/perfusion nozzle 25.

Figure 10:
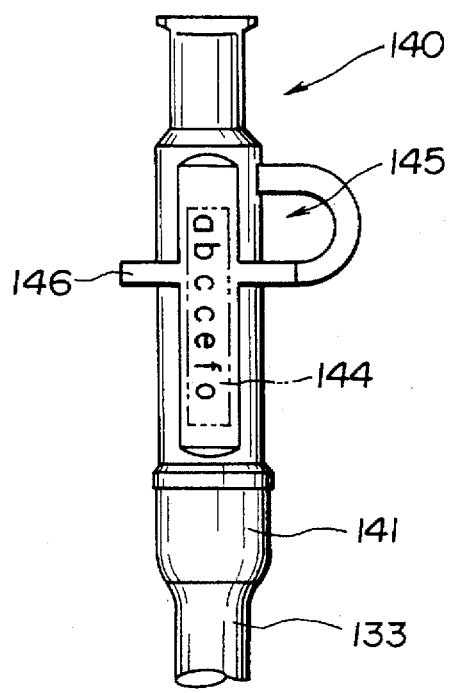
FIG. 10 is a view in a direction of an arrow D in FIG. 6.
Figure 11:
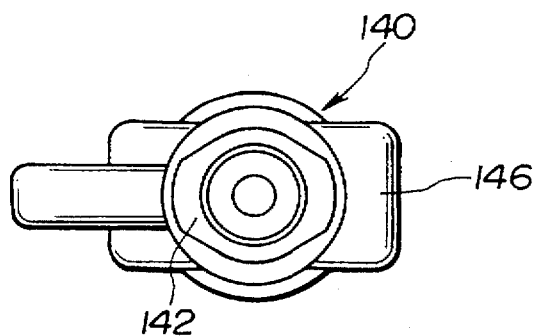
FIG. 11 is a view in a direction of an arrow E in FIG. 9.

As shown in FIGS. 10 and 11, the base member 140 has indicators 144 and 156 for indicating a model name, manufacturer's name, and similar. As shown in FIGS. 9 and 10, a mounting hole 145 is formed so that the base member 140 can be hung for storage or similar. All component parts of the aeration/perfusion channel cleaning adaptor 30 are made of a material such as PSU so that they can be autoclaved. The base member 140 is therefore molded using a resin material of an indication color described in the Operation Manual or similar for indicating that autoclaving is permissible; such as, green. The aeration/perfusion channel cleaning adaptor 30 is durable to disinfectants or ultrasonic cleaning.

Referring to FIGS. 13 to 37, an all-channel cleaning adaptor will be described.

Figure 13:
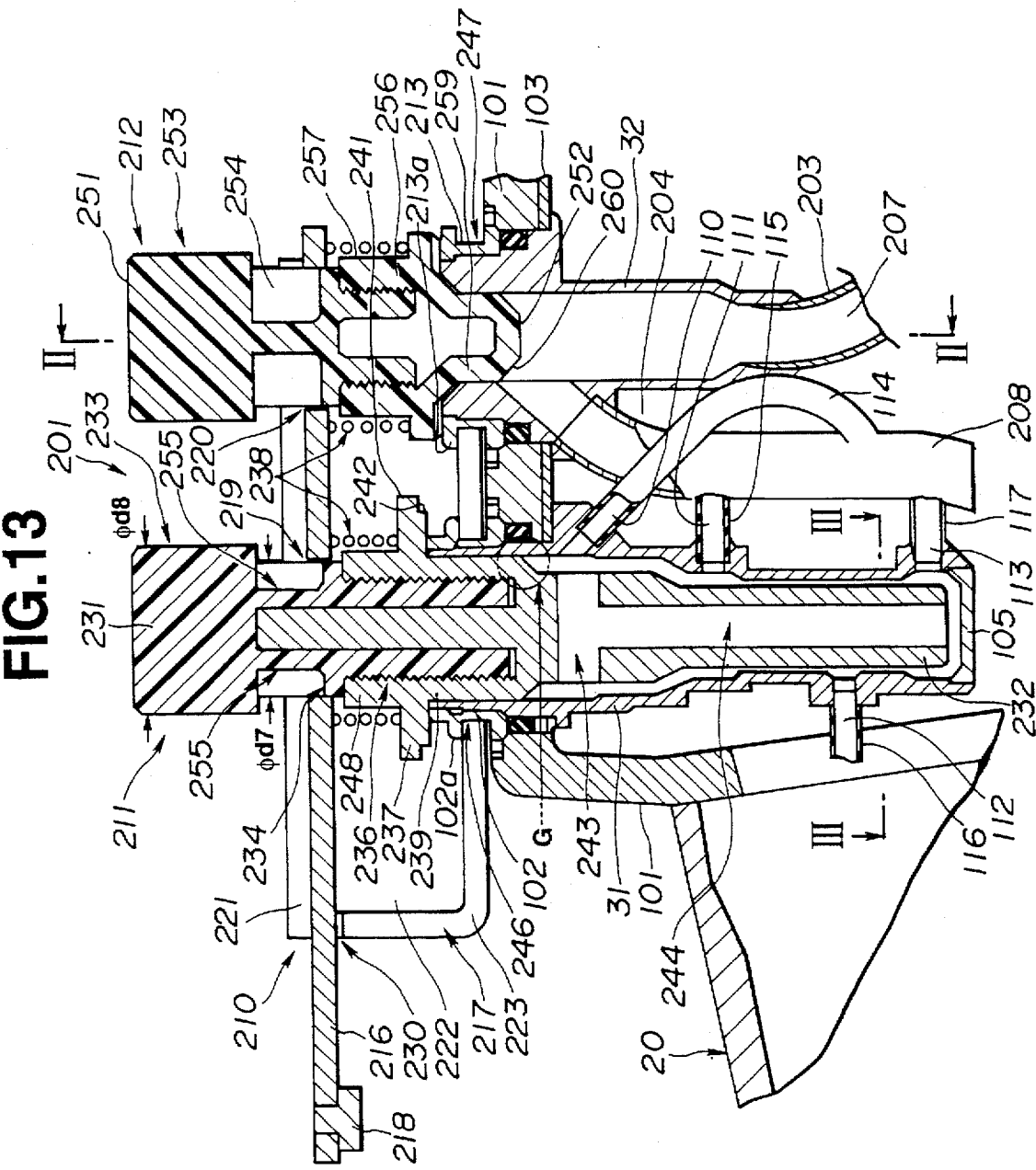
FIG. 13 is a sectional view for explaining an all-channel cleaning adaptor.

Reference numeral 201 in FIG. 13 denotes an all-channel cleaning adaptor serving as a plug means detachable from the operation unit 2 of the endoscope 1. 32 denotes a metallic suction cylinder, similarly to the aeration/perfusion cylinder 31, having a substantially cylindrical shape and being mounted in an opening formed in the body 101 of the operation unit 2 of the endoscope. The suction cylinder 32 is, similarly to the aeration/perfusion cylinder 31, locked in the body 101 with a nut 213 and washer 103 by tightening the nut 213.

An O ring 104 is interposed between the nut 213 and body 101 for ensuring watertightness. Small-diameter sections 246 and 247 whose diameters are ⌀d5 are formed under the flange 102 of the nut 102 and a flange 213a of the nut 213 respectively. The diameters of the flanges 102a and 213a are ⌀d6. The relationship established between the diameters ⌀d5 and ⌀d6 is: ⌀d5<⌀d6.

A metallic connector-side suction pipe 203 is fixed to the bottom of the suction cylinder 32 by soldering, and a metallic suction pipe 204 is fixed to the lateral side thereof by soldering. The connector-side suction pipe 203 constitutes a connector-side suction channel 207 and communicates with the metallic suction base 21 formed on the connector unit 3.

The suction pipe 204 constitutes a distal suction channel 208 and merges into the forceps passage 16a communicating with the suction port 16 formed in the distal section 6 at the distal end of the grip section of the operation unit 2.

The all-channel cleaning adaptor 201 includes a lock assembly 210, an aeration/perfusion plug 211, a suction plug 212, and a plug member 215 detachable from the suction port 16 that will be described later.

Figure 14:
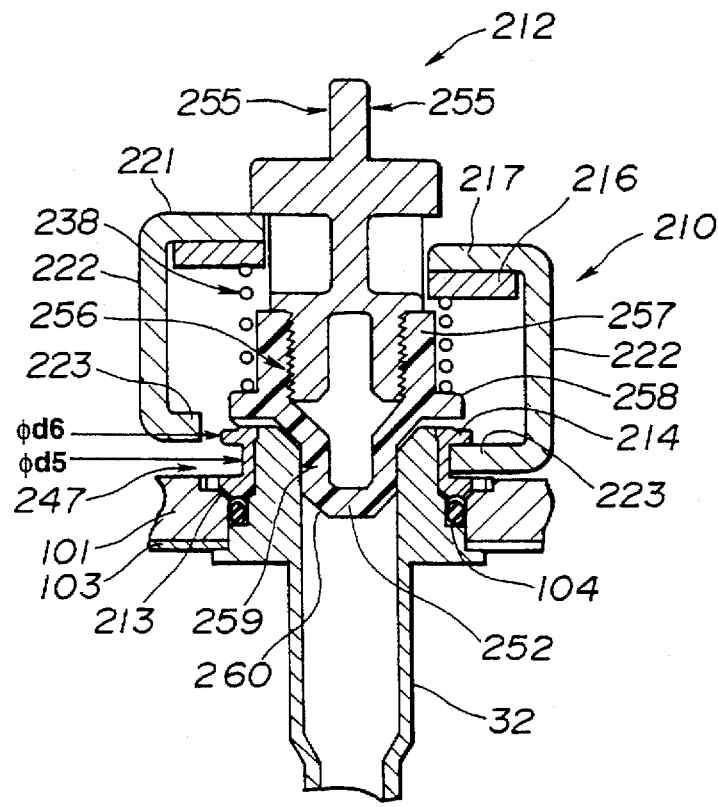
FIG. 14 is an II—II sectional view of FIG. 13.
Figure 15:
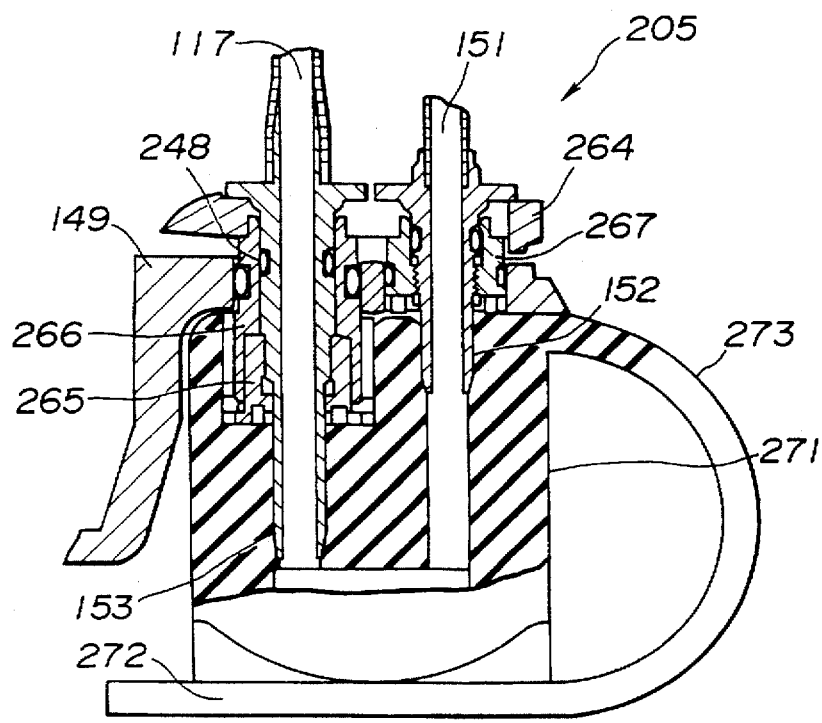
FIG. 15 is a sectional view showing a major portion of a coupling plug.

As shown mainly in FIGS. 13 and 14, the lock assembly 210 includes a flat plate 216 made of a metal such as stainless steel, a housing 217 formed with a metallic plate that has been bent, and a metallic stopper 218. The flat plate 216 has through holes 219 and 220 at positions coinciding with the aeration/perfusion cylinder 31 and suction cylinder 32. The stopper 218 is tightened and then secured using an adhesive so that the housing 217 will not come off from the flat plate 216.

Figure 17:
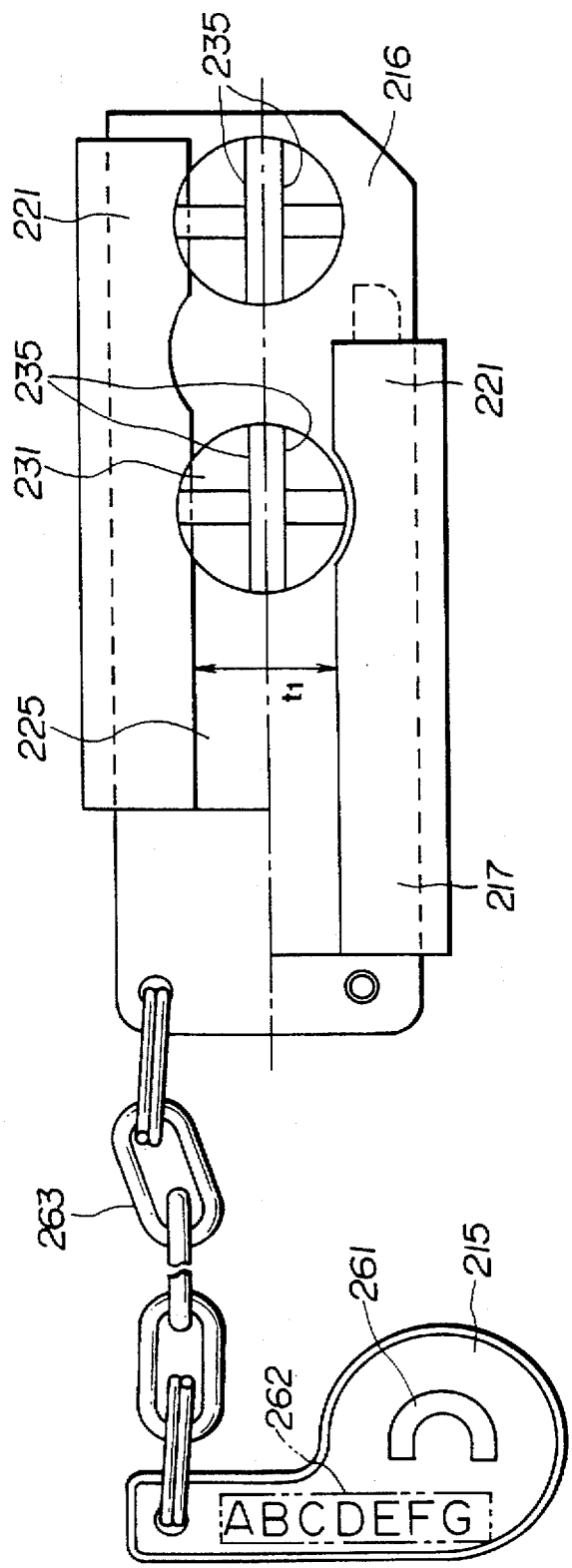
FIG. 17 is a top view of the all-channel cleaning adaptor.
Figure 18:
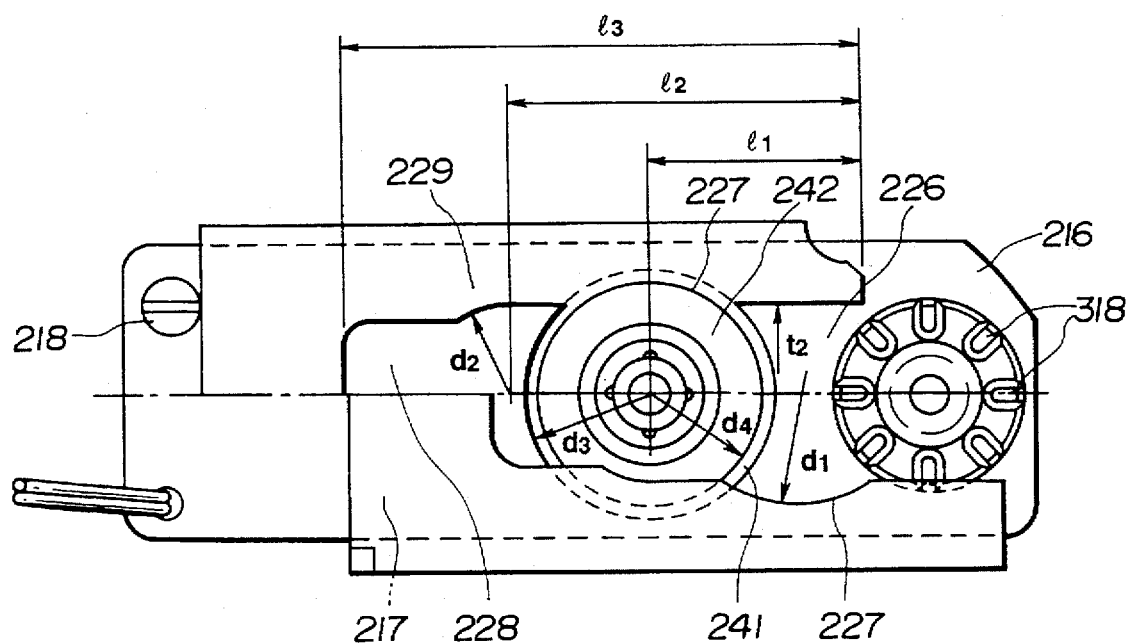
FIG. 18 is a bottom view of the all-channel cleaning adaptor.

As shown mainly in FIGS. 17 and 18, the housing 217 includes: a top surface 221 having a notch 225 of t1 wide extending throughout the overall length thereof; a bottom surface 223 having a notch 226 of t2 wide extending from the lateral end of the suction plug 212 by a length l2, a notch 228 of t2 wide extending from the lateral end of the suction plug 212 by a length l3, arc sections 227 defining a circle of which diameter is ⌀d1 and of which center is separated by a length l1 from the lateral end of the suction plug 212, and arc sections 229 defining a circle whose diameter ⌀d2 is equal to the width t2 and linking notches 226 and 228; and two side surfaces 222 linking the top surface 221 and bottom surface 223. The side surfaces 222 and bottom surface 223 are joined with one another. A clearance 230 whose width is a bit larger than the thickness of the flat plate 216 is created under the top surface 221. The flat plate 216 is locked in the clearance 230.

The aeration/perfusion plug 211 comprises a button 231 made of a rigid resin such as PSU and positioned uppermost, a piston 232 made of a resin such as PSU similarly to the button and inserted in the aeration/perfusion cylinder, and a metallic coil spring 238.

The diameter of the button 231 is larger than that of the through hole 219; and composed of a head 233 having a diameter ⌀d8 and a trunk 234 having a small diameter ⌀d7. The top of the head 233 has the edge thereof chamfered in order to prevent an injury and includes a flat section on which a model name or similar can be inscribed. The piston 232 is tightened and fixed to a thread 236 formed on the trunk 234.

The piston 232 includes a head 248 whose diameter is larger than that of the through hole 219, a flange 237, an engaging section 239, and a bar section 240. The flange 237 is interposed between the flat plate 216 and bottom surface 223, and composed of a large-diameter section 241 and a small-diameter section 242 which are formed in that order adjacently to the head 248. The relationships established among the diameter ød3 of the large-diameter section 241, diameter ød4 of the small-diameter section, and diameter ød1 of the circle defined by the arc sections 227, are as follows: d1<d3, d1≧d4

That is to say, in an unmounted state, the small-diameter section 242 is substantially engaged with the arc sections 227 and positioned. The bottom of the large-diameter section 241 then abuts the top of the bottom surface 233, thus preventing the aeration/perfusion plug 211 from coming off.

The coil spring 238 interposed between the flat plate 216 and flange 237 presses the flange 237 toward the bottom surface 223. In an unmounted state, the flange 237 is pressed toward the bottom surface 223. In a mounted state, the flange 237 is pressed toward the top end of the nut 102.

Figure 19:
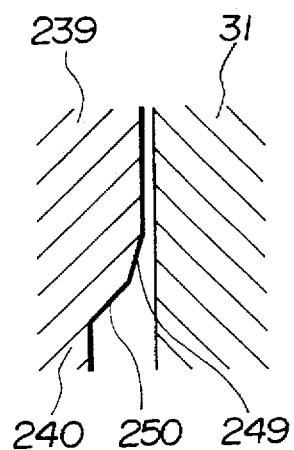
FIG. 19 is a detailed view showing a portion indicated with an arrow G in FIG. 13.

The engaging section 239 is formed below the flange 237. As shown in FIG. 19, in a mounted state, the engaging section 239 substantially engages with the aeration/perfusion cylinder 31. At this time, there is a clearance of 0.05 mm or smaller between the inner circumferential surface of the aeration/perfusion cylinder 31 and the outer circumferential surface of the engaging section 239. A tapered section 249 that is tapered at an acute angle and a tapered section 250 having a larger angle than the tapered section 249 are formed as a diameter-varying section between the engaging section 239 and bar section 240, so that the piston 232 can be inserted in the aeration/perfusion cylinder 31 readily.

The bar section 240 is formed below the engaging section 239. The bar section 240 is structured so that in a mounted state, there will be a clearance ranging from 0.4 mm to 1 mm between the inner circumferential surface of the aeration/perfusion cylinder 31 and the outer circumferential surface of the bar section 240.

Figure 20:
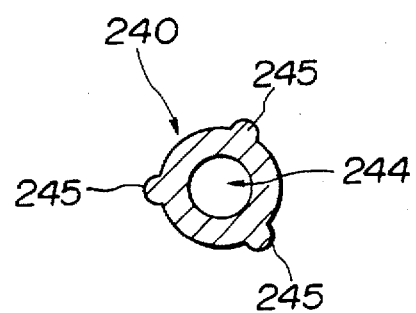
FIG. 20 is an III—III sectional view of FIG. 13.

The bar section 240 has a communication transverse hole 243 that in a mounted state, lies in the vicinity of the opening of the distal aeration channel 114 formed in the aeration/perfusion cylinder 31, and a communication vertical hole 244 communicating with the communication transverse hole 243 and reaching the bottom of the bar section. In the mounted state, therefore, as shown in FIG. 20, at least two juts 245 engage with the inner circumferential surface of the distal perfusion channel 116 so as to determine the radial position of the piston 232 relative to the aeration/perfusion cylinder 31, and then lie between the opening of the distal perfusion channel 116 and the opening of the connector-side perfusion channel 117.

As shown in FIG. 14, the suction plug 212 includes, similarly to the aeration/perfusion plug 211, a button 251 made of a rigid resin such as PSU, a piston 252 made of a resin such as PSU similarly to the button, and a metallic coil spring 238 similar to the one of the aeration/perfusion plug 211.

The outer diameter of the button 251 is larger than that of the through hole 220, and composed of a head 253 having a diameter ød8 and a trunk 254 having a small diameter ød7. The top of the head 253 has the edge thereof chamfered for the purpose of preventing an injury, and includes a flat section 255 on which a model name or the like can be inscribed. The piston 252 is tightened and fixed to a thread 256 formed on the trunk 254.

The piston 252 includes a head 257 whose diameter is larger than that of the through hole 220, a flange 258, and an engaging section 259. A coil spring 238 is interposed between the flat plate 216 and flange 258. The coil spring 238 presses the flange 258 toward the bottom surface 223. In an unmounted state, the coil spring 238 presses the flange 258 toward the bottom surface 223. The head 253 is therefore pressed to the flat plate 216, thus preventing the suction plug 212 from coming off. In a mounted state, the flange 258 is pressed toward the top end of the nut 213.

At least one notch 318 is formed in the bottom of the flange 258, thus improving drainage efficiency for cleaning of the all-channel cleaning adaptor.

The engaging section 259 is formed below the button 251. In a mounted state, the engaging section 259 substantially engages, similarly to the one shown in FIG. 19, with the suction cylinder 32. A clearance of 0.05 mm or smaller is then created between the inner circumferential surface of the suction cylinder 32 and the outer circumferential surface of the engaging section. A tapered section 260 is formed below the engaging section 259, thus assisting in inserting the piston 252 into the suction cylinder 32.

As shown in FIG. 17, the plug 215 is mounted in the forceps inlet 16 distal to the operation unit 2 of the endoscope 1, and composed of a leakage hole 261 and an indicator 262 on which a model name or similar can be inscribed. When a liquid slightly leaks out from the leakage hole 261, the forceps inlet 16 is filled with the liquid. The plug 215 may be joined with the flat plate 216 by a chain 263 or similar made of plastic or stainless steel. The overall length of the chain 263 is set to a length permitting easy mounting of the plug 215 in the forceps inlet 16, but not interfering with the mounting. The junction between the plug 215 and chain 263 is positioned off the center of the portion of the plug 215 mounted in the forceps inlet 16. This is intended to make the plug 215 smaller.

The procedure of mounting the all-channel cleaning adaptor 201 in an endoscope will be described.

First, the aeration/perfusion plug 211 is inserted in the aeration/perfusion cylinder 31, and the suction plug 212 is inserted in the suction cylinder 32. While being pushed down along the axes of the aeration/perfusion plug 211 and suction plug 212, the lock assembly 210 is moved from the aeration/perfusion cylinder 31 toward the suction cylinder 32. At this time, the relationship established among the dimensions relating to the notch 226, small-diameter sections 246 and 247, and flanges 102a and 213a is:

d6>t2≧d5.

The following relationship is set up between the dimensions relating to the head 233, trunk 234, and notch 226: d8>t1>d7. The bottom surface 223 therefore moves along the small-diameter sections 246 and 247 of the nut 102 and suction plug 213.

The dimensions d2 and t2 have the following relationship: d2=t2. The bottom surface 223 is therefore positioned and immobilized at a position at which the arc sections 229 abut on the small-diameter section 246.

A distance by which the housing 217 has moved from a position in a unmounted state to a position in a mounted state is 14. The moved distance 14 equals to a value calculated by subtracting a distance 11 from a distance 12. The value of the distance 12 is set so that when a movement is made by the distance 14, the head 248 will lie at a position not interfering with the edge of the notch 228.

As mentioned above, the mounted all-channel cleaning adaptor 201 can inject a cleaning solution or similar from the connector-side aeration channel 115, connector-side perfusion channel 117, and connector-side suction channel 207, which are extending toward the connector unit, into the distal aeration channel 114, connector-side aeration channel 115, distal perfusion channel 116, connector-side perfusion channel 117, pressurization channel 151, connector-side suction channel 207, distal suction channel 208, and forceps passage 16a which are running through the endoscope 1. The heads 248 and 257 are provided with a stopper for fear the aeration/perfusion plug 211 and suction plug 212 might pop out from the aeration/perfusion cylinder 31 and suction cylinder 32 due to the pressure applied when the cleaning solution or similar is injected.

As described with reference to FIG. 19, a clearance of 0.05 mm or smaller is preserved between the inner circumferential surface of each cylinder and the outer circumferential surface of each engaging section. A cleaning solution can therefore enter the clearances.

When the outer diameter of a projection and the inner diameter of an aeration/perfusion cylinder engaging with the projection are varied depending on a model, a cleaning instrument of an incorrect model will not be mounted by mistake.

All components of an all-channel cleaning adaptor are made of materials permitting autoclaving. The all-channel cleaning adaptor can therefore be autoclaved. The button 231 or 251 is molded using a resin of an indication color that is described in advance in the Operation Manual or similar in order to visually indicate that autoclaving is permissible, for example, green. The all-channel cleaning adaptor is durable to not only autoclaving but also disinfectant solutions and ultrasonic cleaning.

A communication vertical hole and communication transverse hole are formed in order to remove bubbles occurring in the channels when an all-channel cleaning adaptor is used to flow a disinfectant solution into all channels. The bubbles are readily removed through the communication vertical hole and communication transverse hole.

A perfusion base 153 abuts on a connector body 264 for securing a connector unit 149. By tightening a nut 265 relative to the perfusion base 153, the perfusion base 153 is pressed and fixed to the connector body 264 together with a locking member 266.

A pressurization base 152 also abuts on the connector body 264. By tightening a nut 267 relative to the pressurization base 152, the pressurization base 152 is pressed and fixed to the connector body 264.

An O ring is placed at each of given positions between the nut 265 and locking member 266, between the locking member 266 and connector unit 249, between the pressurization base 152 and nut 267, and between the nut 267 and connector unit 249 in order to ensure watertightness.

Figure 21:
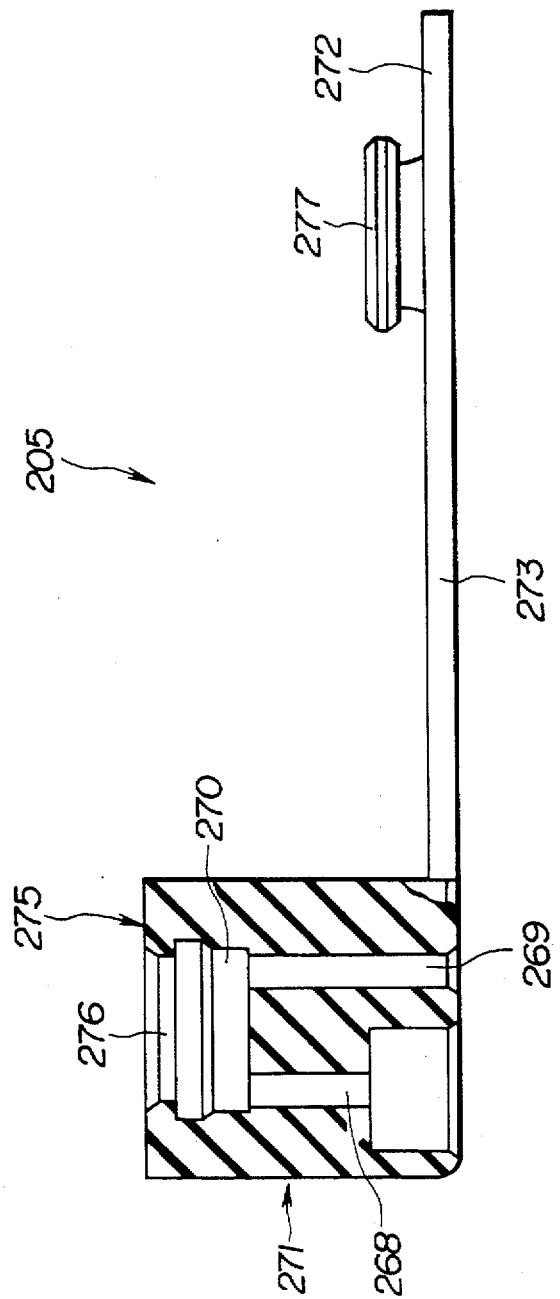
FIG. 21 is a sectional view showing a major portion of the coupling plug that is developed.
Figure 22:
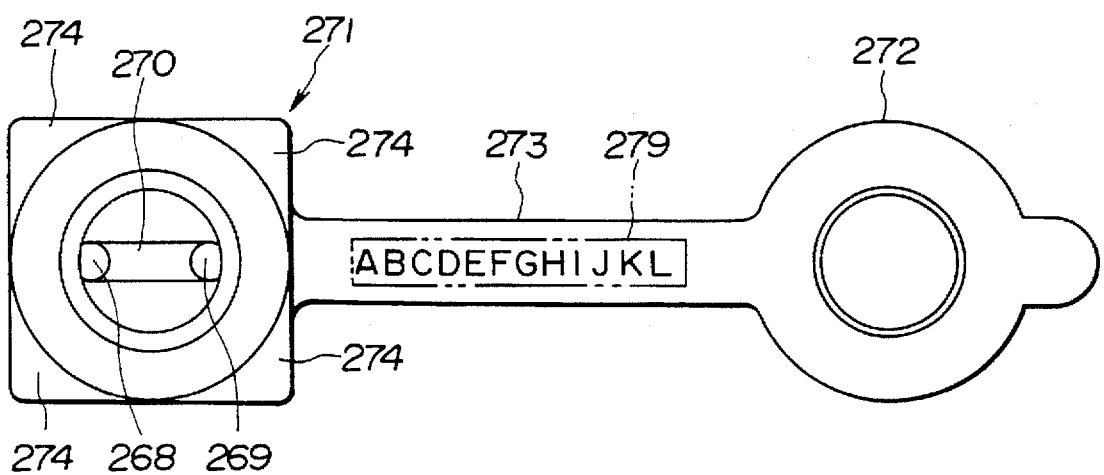
FIG. 22 is a top view showing the coupling plug that is developed.
Figure 23:
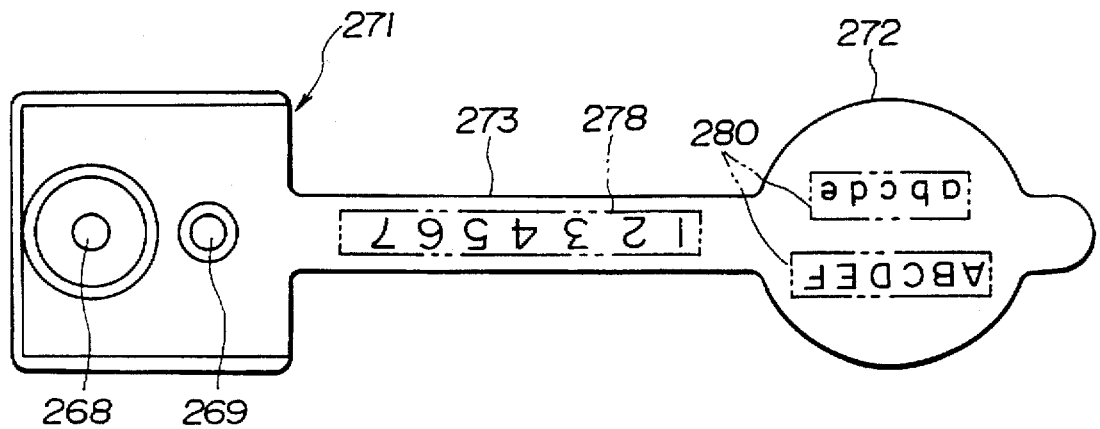
FIG. 23 is a bottom view showing the coupling plug that is developed.

As shown in FIGS. 21 to 23, a coupling plug 205 includes a main unit 271, a lid 272, and a coupling member 273 for coupling the main unit 271 and lid 272. Each crest of the main unit 271 has a curved surface of about 0.5 mm in radius. The main unit 271 having a substantially square top is shaped like a rectangular parallelepiped. Conical surfaces 274 are formed in the vicinity of a circular top.

Internally, the main unit 271 includes: a perfusion channel 268 whose diameter is smaller by about 0.2 mm to 0.4 mm than the outer diameter of the perfusion base 153 and which communicates with the perfusion base 153; an aeration channel 269 of which diameter is the same as that of the perfusion channel 268 having a diameter that is smaller by about 0.2 mm to 0.4 mm than the outer diameter of the pressurization base 152 and which communicates with the pressurization base 152, a coupling channel 270 that has a square cross section, of which one side is substantially equal to the outer diameters of the perfusion channel 268 and aeration channel 269, and that communicates with the perfusion channel 268 and aeration channel 269; a seal 275 that is attached circumferentially in order to ensure watertightness in cooperation with the lid 272 and that reaches the upper part of the coupling channel 270; and a communication hole 276 of which diameter is smaller than that of the seal 275 and which allows the seal 275 to reach the top end surface.

A seal 277 whose diameter is larger by about 0.2 mm to 0.4 mm than that of the seal 275 of the main unit 271 projects outwardly from the lid 272. When the seal 277 is press-fitted onto the seal 275, the a watertight seal between the coupling channel 270 and the top of the main unit 271 is ensured due to elastic deformation of rubber. In this state, the perfusion channel 268 in the coupling plug 205 is connected to the perfusion base 153 by utilizing elastic deformation of rubber, and the perfusion channel 269 is connected to the pressurization base 152 by utilizing elastic deformation of rubber. This causes the connector-side perfusion channel 117 and connector-side aeration channel 115 to communicate with each other. At the same time, the a watertight seal relative to the outside is ensured.

The coupling plug 205 is made of silicon rubber and can be autoclaved. Since the channels are reaching the top and bottom of the coupling plug, when the coupling plug 205 itself is cleaned, the coupling member 273 of the coupling plug 205 can be cleaned readily using a brush or similar that is not shown. The coupling plug 205 may be secured watertightly with the lid 272 mounted on the main unit 271. As shown in FIGS. 22 and 23, the coupling plug 205 has indicators 278, 279, and 280 for indicating a model name or the fact that autoclaving is permissible.

Figure 16:
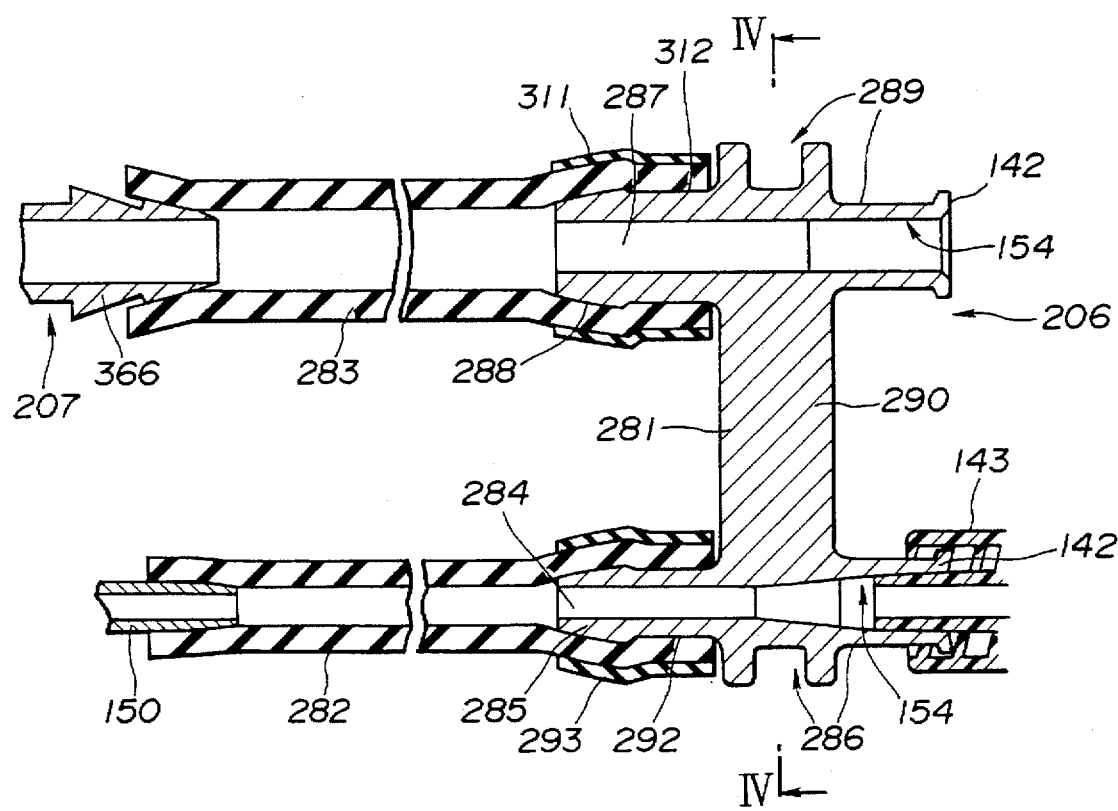
FIG. 16 is a sectional view showing a major portion of an injection tube assembly.

As shown in FIG. 16, an injection tube assembly 206 is a tube assembly for injecting a liquid such as a cleaning solution to the distal aeration channel 114, connector-side aeration channel 115, distal perfusion channel 116, connector-side perfusion channel 117, pressurization channel 151, connector-side suction channel 207, distal suction channel 208, and forceps passage 16a, which are incorporated in the endoscope 1, through an aeration base 150 or suction base 366 which is opening in the connector unit 149.

The injection tube assembly 206 includes a main unit 281 made of a rigid resin such as PSU, an aeration/perfusion channel tube 282 made of silicon rubber or similar and provided with a small-diameter channel, and a suction channel tube 283 made of silicon rubber or similar and provided with a large-diameter channel.

The main unit 281 includes: a first cylindrical section 286 having a substantially cylindrical shape, having a small-diameter channel 284 penetrating therethrough, having a projection 285 to which the aeration/perfusion channel tube 282 can be connected formed as one end portion thereof, and having, similarly to the aeration/perfusion channel cleaning adaptor 30, a lure pawl 142 and tapered section 154, which are used to connect a syringe 143 or similar, formed as the other end portion thereof; a second cylindrical section 289 having a substantially cylindrical shape, having a large-diameter channel 287 penetrating therethrough, having a projection 288, to which the suction channel tube 283 is connected, formed as one end portion thereof, and having a lure pawl 142 and tapered section 154, which are used to connect the syringe 143 or similar, formed as the other end portion; and a coupling section 290 for coupling the first cylindrical section 286 and second cylindrical section 289. The coupling section 290 has, as shown in FIG. 24, flat sections 291 on which a model name or similar can be inscribed.

For the connection of the projection 285 and aeration/perfusion channel tube 282, the aeration/perfusion channel tube 282 is press-fitted onto a small-diameter section 292 of the projection 285, and then the outer circumference of the portion of the aeration/perfusion channel tube 282 resting on the projection 285 is covered with a heat-contractive tube 293. At this time, when a close-winding metallic coil, which is not shown, is pressed and fixed to the outer circumference of the heat-contractive tube 293, fixing strength can be increased.

For connecting the suction channel tube 283 to the projection 288, similarly to the aeration/perfusion channel tube 282, the suction channel tube 283 is press-fitted onto a small-diameter section 312 of the projection, and then the outer circumference of the portion of the suction channel tube 283 resting on the projection 288 is covered with a heat-contractive tube 311. At this time, when a close-winding metallic coil, which is not shown, is pressed and fixed to the outer circumference of the heat-contractive tube 311, fixing strength can be increased.

The aeration/perfusion channel tube 282 of the injection tube assembly is detachably connected to the body 101, the suction channel tube 283 is detachably connected to the connector-side suction channel 207, and a syringe or similar is detachably connected to either the first cylindrical section 286 or second cylindrical section 289 selectively, whereby a fluid can be injected selectively to the distal aeration channel 114, connector-side aeration channel 115, distal perfusion channel 116, connector-side perfusion channel 117, and pressurization channel 151 in the endoscope, or to the connector-side suction channel 207, distal suction channel 208, and forceps passage 16a therein.

The aeration/perfusion channel tube 282 and suction channel tube 283 are designed to have a length not hindering the work of flowing a cleaning solution or similar. The aeration/perfusion channel tube 282 is made longer than the suction channel tube 283. For example, the aeration/perfusion channel tube 282 is approximately 40 cm long, and the suction channel tube 283 is approximately 50 cm long.

Since each of the cylindrical sections 286 and 289 has the lure pawl 142 and tapered section 154, something having the same structure as the distal portion of a syringe, for example, an injection adaptor or drainage adaptor, which will be described later, can be connected.

Both the lure pawls 142 for the aeration/perfusion channel and suction channel have the same shape, and have a hook section in the same direction as shown in FIG. 16. A syringe 143 or injection adaptor 295 can be attached or detached in the same manner.

The injection tube assembly 206 is made of a material permitting autoclaving and can therefore be autoclaved. The aeration/perfusion channel tube 282 and suction channel tube 283 are provided with an indicator for identification, for example, a tag or similar that is not shown in order to prevent incorrect assembling. A hole may be bored in the coupling section 290 and lid 272 so that the coupling section 290 and lid 272 can be joined with each other by the chain 263 or similar. Moreover, the all-channel cleaning adaptor 201 may be provided with a tag or similar indicating that the adaptor should be mounted in an endoscope.

An injection adaptor 295 shown in FIG. 25 is an injection adaptor that can be detachably attached selectively to the channel 284 or 287 of the injection tube assembly 206. The injection adaptor 295 includes a main unit 296, a metallic filter unit 297, and a tube 298 made of silicon rubber for joining the main unit 296 with the metallic filter unit 297.

The main unit 296 has the same structure as, for example, a distal portion 294 of the syringe 143, and includes: a connecting section 299 that is made of a rigid resin such as PSU and has a channel 300 inside thereof; a through channel 301 in one end of which the connecting section 299 is locked; a branch tube 303 being made of a rigid resin such as PSU and having a channel 302 branching out from the through channel 301 passed therethrough; a projection 304 which is made of a rigid resin such as PSU, to which the tube 298 is connected, which is fixed to a branch channel of the branch tube 303, and which has a channel 305 formed inside thereof; and balls 306 that are made of a non-corrosive metal such as stainless steel, interposed between the distal portion 294 and branch tube 303 and between the branch tube 303 and projection 304 respectively so that the balls can slide, and have larger diameters than the channels 300 and 302 respectively.

Figure 26:
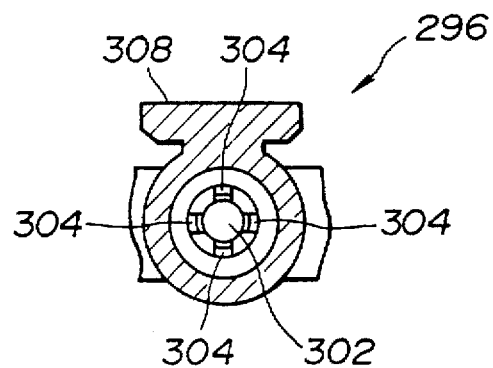
FIG. 26 is a V—V sectional view of FIG. 25.
Figure 27:
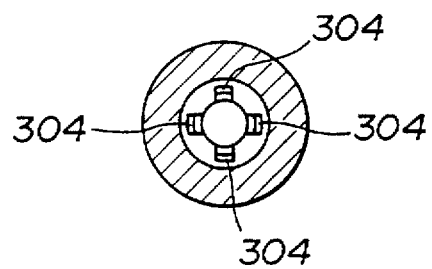
FIG. 27 is a VI—VI sectional view of FIG. 25.

In the vicinity of an end of the through channel 301 of the branch tube 303 locked in the distal portion 294, a tapered section 307 whose diameter increases toward the end of the branch tube 303 is formed. As shown in FIG. 26, at least one jut 308 is formed in the vicinity of an end of the channel 302 locked in the projection 304. In the vicinity of an end of the channel 305 of the projection 304 locked in the branch tube 303, a tapered section 307 whose diameter increases toward the end of the projection is formed. As shown in FIG. 27, at least one jut 304 is formed in the vicinity of an end of the channel 300 locked in the branch tube 303 in the distal portion 294.

In the main unit 296 having the aforesaid structure, when a liquid such as a cleaning solution is about to flow from the through channel 301 toward the channel 300, the ball 306 abuts the juts 304. The cleaning solution therefore flows from the through channel 301 to the channel 300 via any passage other than the abutment. When a cleaning solution or similar flows from the through channel 300 toward the channel 301, the ball 306 abuts on the tapered section 307 to block the through channel 301. The cleaning solution does therefore not flow.

Likewise, when a liquid such as a cleaning solution flows from the channel 305 toward the channel 302, the ball 306 abuts the juts 304. The cleaning solution therefore flows from the channel 305 toward the channel 302 via any passage other than the abutment. When a cleaning solution flows from the channel 302 toward the channel 305, the ball 306 abuts on the tapered section 307 to block the channel 302. The cleaning solution does therefore not flow.

A lure pawl 142 and tapered section 154 are, similarly to those of the aeration/perfusion channel cleaning adaptor or injection tube assembly 206, formed at the other end of the through channel 301 of the main unit 296. The syringe 143 can be detachably connected to the other end of the through channel, thus enabling a liquid such as a cleaning solution in the syringe 143 to flow from the channel 305 toward the channel 300.

Figure 28:
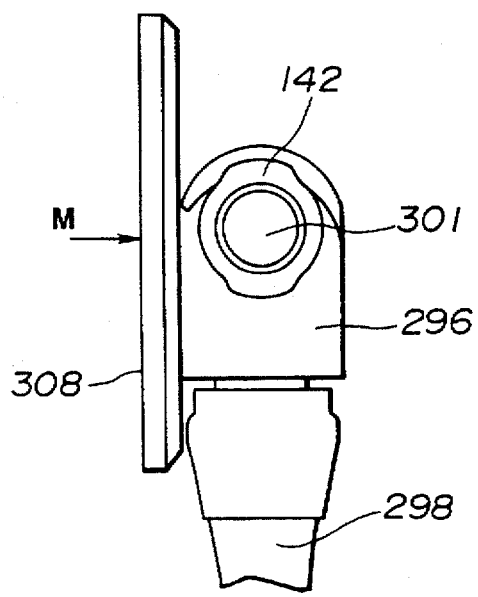
FIG. 28 is a view showing the injection adaptor on the side thereof to which a syringe is connected.
Figure 29:
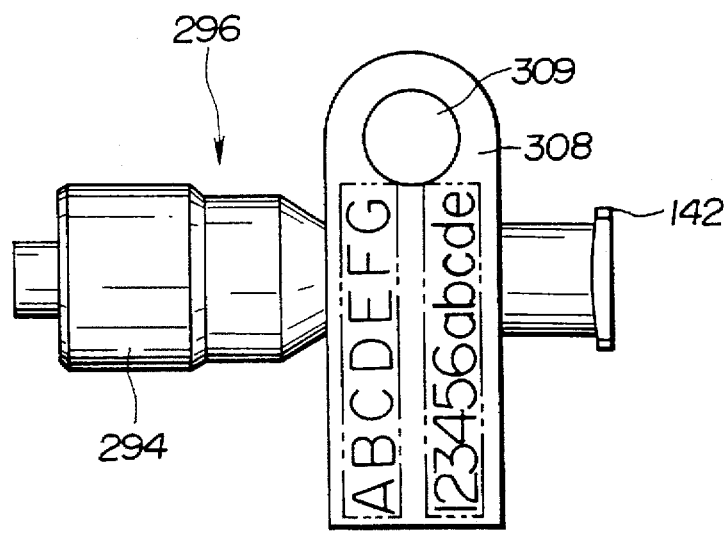
FIG. 29 is a view in a direction of an arrow M in FIG. 28.

As shown in FIG. 28, the main unit 296 has a flat section 308 as a united part thereof. A model name or similar can be inscribed on the flat section 308. When a through hole 309 is, as shown in FIG. 29, bored in the flat section 308, the through hole 309 can be used to hang the main unit 296 for storage or to join the main unit with another cleaning instrument by means of a string or the like.

Figure 30:
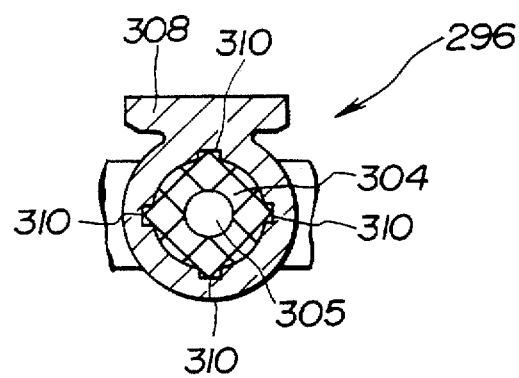
FIG. 30 is a VII—VII sectional view of FIG. 25.

As shown in FIG. 30, at least one detent 310 is formed in an area of the main unit 296a in which the projection 304 is locked in order to increase locking force. The same applies to another area of the main unit 296 in which the distal portion 294 is locked.

The tube 298 is then fixed to the projection 304 in the same manner as that the aeration/perfusion channel tube 282 of the injection tube assembly 206 is connected to the projection 285 using the heat-contractive tube 313. The other end of the tube 298 is connected to a projection 314 of the filter unit 297. At this time, an adhesive is applied between the tube 298 and projection 304 or 314 in order to fix the tube 298. The fixing strength further improves.

The filter unit 297 includes a channel 315 penetrating therethrough. A metallic filter 316 for removing waste threads, dust, and similar from a cleaning solution, disinfectant solution, or rinsing solution is locked in the middle of the channel 315. The metallic filter 316 may be a fiber mesh and detachably locked in the filter unit 297.

At least one notch 317 is formed in the end surface of the filter unit 297. When a liquid such as a cleaning solution is sucked into the syringe 143, the filter unit 297 must be fully immersed in the liquid. The filter unit 297 is therefore made of a metal which is expected to act as a weight. The filter unit 297 thus fully sinks in the liquid.

When the filter unit 297 sinks in a liquid, if the end surface of the filter unit 297 hits against the wall of a vat or similar that is filled with a cleaning solution or similar, the filter unit 297 will not be blocked owing to the notch 317. The cleaning solution can therefore be sucked reliably.

The injection adaptor 295 is made of a material permitting autoclaving and can therefore be autoclaved. The injection adaptor 295 can be detachably connected to the injection tube assembly 206 or aeration/perfusion channel cleaning adaptor. The injection adaptor 295 has a length not interfering with the work of flowing a cleaning solution or similar.

The aeration/perfusion channel tube 282 or suction channel tube 283 of the injection tube assembly 206 is thick enough not to be blocked but to retain the substantially circular cross section even when sucked by the suction unit 55 via a drainage adaptor 350 or 360, which will be described later, and thus applied negative pressure. It is also possible to make an attempt to reduce the frequency of worker's manipulating the syringe 143 by connecting the suction channel tube 283 to the aeration/perfusion channel tube 282 whose inner diameter is smaller in the middle of the suction channel tube 283 in order to reduce the amount of liquid remaining in the tube. Furthermore, the number of the tapered sections 154 of the injection tube assembly 206 to which the syringe 143 can be connected may be diminished to one, and the injection tube assembly 206 is shaped like a Y-shaped adaptor, which will be described later, shown in FIG. 37, so that a liquid can be injected simultaneously to both the the aeration/perfusion channel tube 282 and suction channel tube 283. However, in this case, consideration must be taken into the balance of fluids flowing into the aeration/perfusion channel and suction channel in the endoscope 1. For causing a fluid to reliably flow into both the channels, an orifice 369 is formed or the inner diameters and lengths of the aeration/perfusion channel tube 282 and suction channel tube 283 are optimized.

Figure 31:
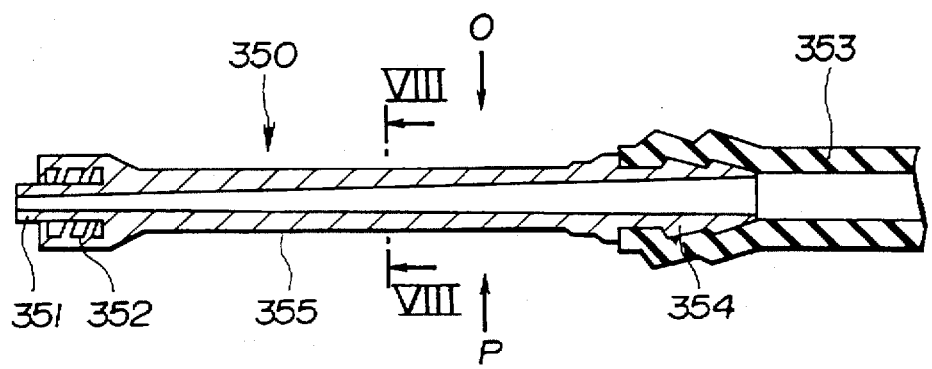
FIG. 31 is a sectional view of a drainage adaptor.

As shown in FIG. 31, one end portion of a drainage adaptor 350 has the same male lure-lock shape as the distal portion of the syringe 143 or injection adaptor 295. The end portion thereof has a syringe tapered section 351 inside thereof. A female thread 352 having two ridges and engaging with the lure pawl 142 is formed along the outer circumference of the end portion (See FIG. 16).

The other end portion of the drainage adaptor 350 has a tapered tube connecting section 354 to which a thick suction tube 353 being made of a soft material such as silicon and having a diameter of about 6 mm can be attached watertightly. A grip section 356 having a communication hole 355 inside thereof is interposed between the syringe tapered section 351 and tube connecting section 354. The inner diameter of the communication hole 355 gradually increases as the communication hole 355 goes from the syringe tapered section 351 toward the tube coupler 354. This shape hinders dirt from clogging the communication hole 355.

Figure 32:
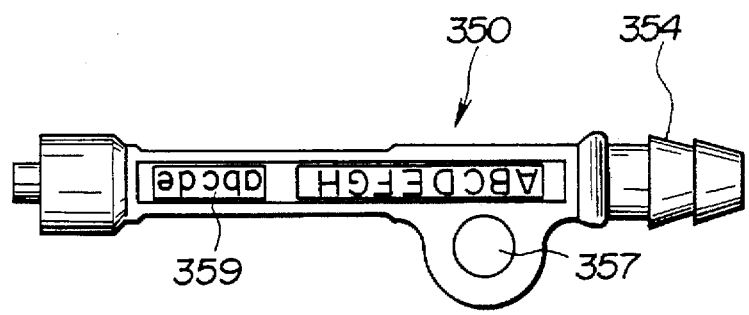
FIG. 32 is a view in a direction of an arrow O in FIG. 31.
Figure 33:
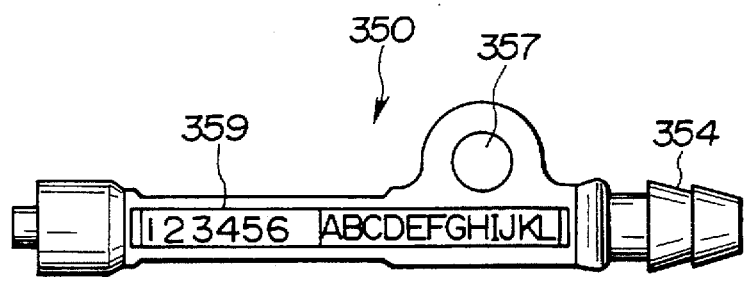
FIG. 33 is a view in a direction of an arrow P in FIG. 31.
Figure 34:
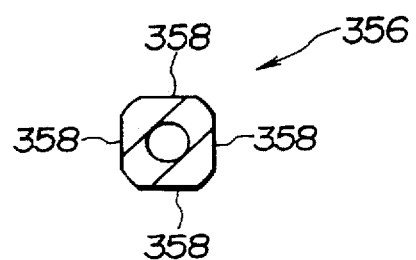
FIG. 34 is a VIII—VIII sectional view of FIG. 31.

In the middle of the grip section 356, a hook hanging hole 357 enabling the drainage adaptor to be hung on a locally-procurable hook or similar or to be joined with another cleaning instrument by a string or similar is formed. The length of the grip section 356 is set to a length allowing a worker to grip the drainage adaptor and attach or detach the drainage adaptor easily. Specifically, the length ranges from 5 cm to 15 cm. The grip section is, as shown in FIG. 34, provided with four flat surfaces 358 in an effort to hinder the drainage adaptor from sliding in a worker's gripping hand. On two of the flat surfaces, an indicator 359, which is shown in FIG. 32 or 33, is formed to inscribe a product number, manufacturing country, manufacturer, or information concerning whether or not autoclaving is permissible.

Figure 35:
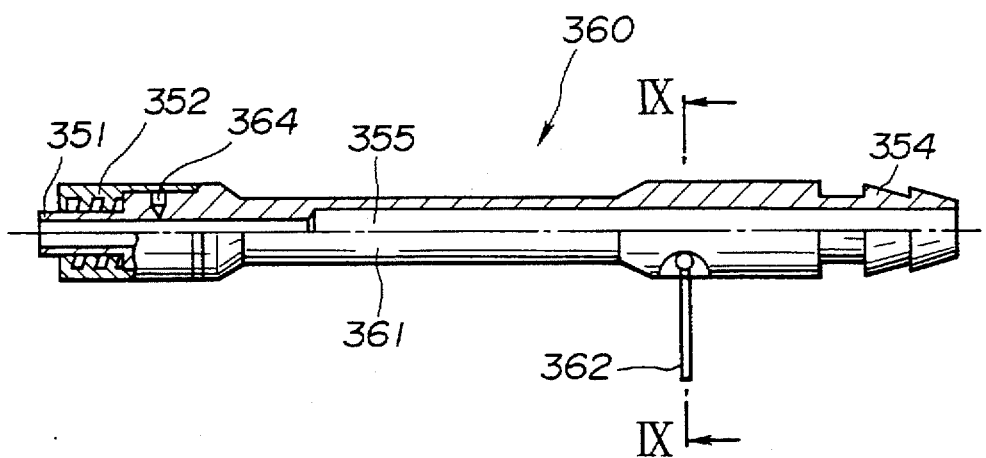
FIG. 35 shows another structure of a drainage adaptor.
Figure 36:
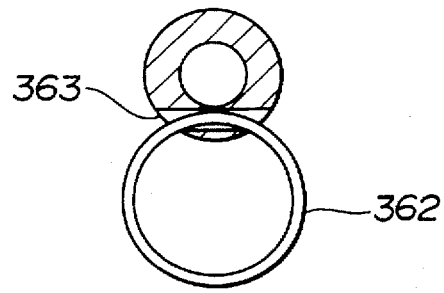
FIG. 36 is an IX—IX sectional view of FIG. 35.

Referring to FIGS. 35 and 36, another structure of a drainage adaptor will be described.

A drainage adaptor 360 is an assembly in which a body 361 is made of an anti-corrosion metal such as stainless steel and made by uniting a syringe tapered section 351, tube connecting section 354, and communication hole 355, and in which a female thread 352 and a ring 362 defining a hook hanging hole 357 are provided separately from the body 361 and mounted on the the body 361. The ring 362 is made by machining a wire made of a metal such as stainless steel in the form of a ring, and loosely inserted in a ditch 363 formed in the body so that the ring 362 can be detached. The female thread 352 may be attached to the body 361 using an adhesive or detachably coupled to the body 361 using a coupling member 364 such as a screw. Thus, since the body, female thread, and ring are detachable, if any of the three components should be broken, it can be replaced with a new one readily.

Figure 37:
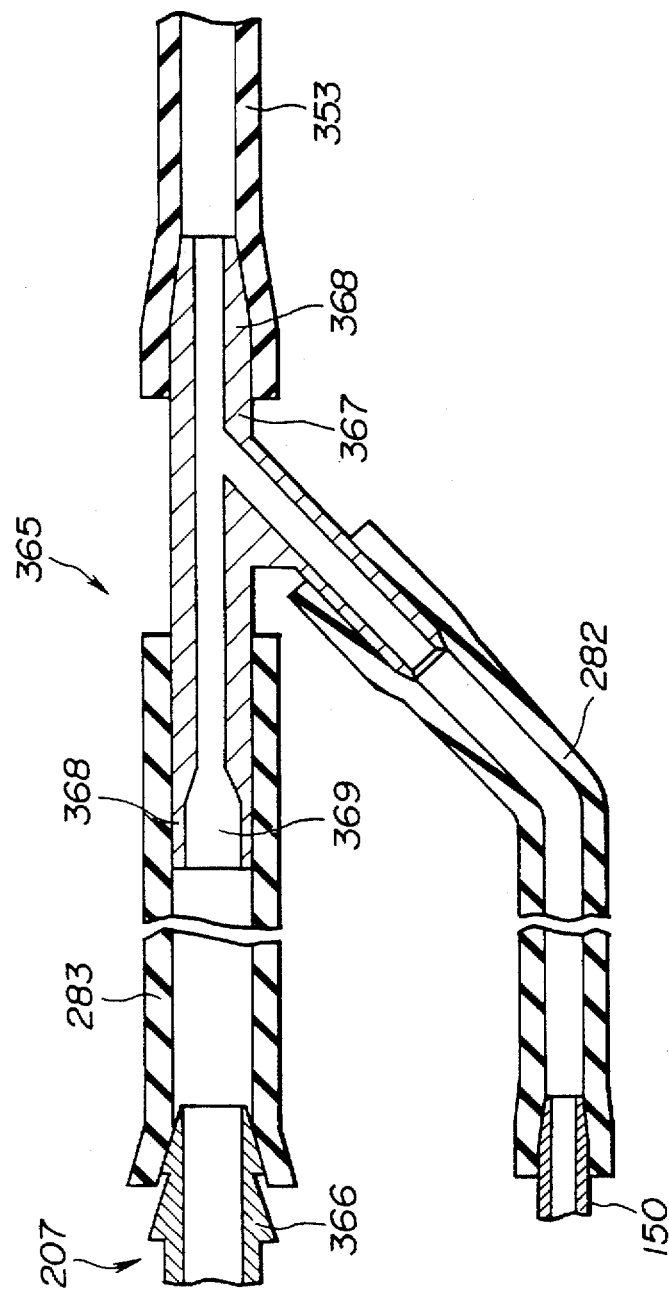
FIG. 37 shows another structure of a drainage adaptor.

Referring to FIG. 37, a drainage adaptor having another structure will be described.

A drainage adaptor 365 includes, similarly to the injection tube assembly 206, an aeration/perfusion channel tube 282 to be press-fitted onto the aeration base 150 on the connector unit 149 watertightly, and a suction channel tube 283 to be watertightly press-fitted onto the suction base 366 for the connector-side suction channel 207. The tubes 282 and 283 are watertightly engaged with and fixed to a Y-shaped adaptor 367 in which two channels are merged into one channel. The other end portion of the Y-shaped adaptor 367 has a tube connecting section 368 having the outer circumferential surface thereof tapered. Similarly to the one shown in FIG. 31, the suction tube 353 can be attached or detached readily and watertightly. An orifice 369 for use in correcting the drainage performances such as drainage speeds of the aeration/perfusion channel tube 282 and suction channel tube 283 is bored in the tube connecting section 368 of the Y-shaped adaptor 367.

By employing the drainage adaptor 350, 360, or 365, a liquid remaining in the aeration channel, perfusion channel, or suction channel, a liquid remaining in a forceps raise wire guide tube in an endoscope having a forceps raiser; such as, a lateral-view endoscope, or a liquid remaining in an endoscope having a forward perfusion channel can be drained off. The drainage adapters may be changed to select the one most suitable for a connecting section of an endoscope.

By employing the drainage adaptor 365, liquids remaining in a plurality of channels can be drained off with one suction. This relieves a worker from annoying work. The plurality of channels are not limited to two channels. Alternatively, a drainage adaptor may be structured to merge three or more tubes into one tube, so that the drainage adaptor can be joined with the proximal base of a forceps raise wire guide tube or forward perfusion channel.

The present invention is not limited to the aforesaid embodiments. On the contrary, the lengths, thicknesses, and rigidities of tubes may be varied so that examination can always be conducted using a clean endoscope permitting excellent workability for cleaning the endoscope using each cleaning instrument. Moreover, separate cleaning instruments may be integrated into a simple unit. Various variants are feasible.

In the present invention, it will be apparent that a wide range of embodiments can be formed on the basis of the invention without a departure from the scope and spirit of the invention. The present invention is limited to the appended claims but not restricted to any specific embodiments.

What is claimed is:

1. An endoscope system, comprising:
   an endoscope having an insertional part, an operation unit, and a connector unit wherein said connector unit is connected to said operation unit via a universal chord including tubes and said insertional part is connected to said operation unit via channels, said insertional part having a distal section, wherein said distal section has an opening formed therein for communicating with said operation unit via said channels; and
   at least one cleaning means for cleaning out any one of a group consisting of said tubes between said connector unit and said operation unit and said channels between said insertional part and said operation unit, said cleaning means having a flexible tube that can be connected to an opening formed in any one of a group consisting of said operation unit and said connector unit of said endoscope via an adaptor and said flexible tube having an overall length of greater than or equal to 30 cm or larger.

2. The endoscope system according to claim 1, wherein said cleaning means is a syringe such that a tapered section of a distal portion of said syringe and at least one end of said flexible tube can be connected to each other watertightly.

3. The endoscope system according to claim 2, wherein said syringe connected to said second end of said flexible tube has a capacity ranging from 30 ml to 50 ml.

4. The endoscope system according to claim 2, wherein said overall length of said flexible tube is between 30 to 70 cm.

5. The endoscope system according to claim 2, wherein said flexible tube communicates with at least one of a group consisting of an aeration channel, a perfusion channel, a aeration tube and a perfusion tube.

6. The endoscope system according to claim 1, wherein at least one end of said flexible tube is provided with a weight.

7. The endoscope system according to claim 6, wherein said overall length of said flexible tube between 30 to 70 cm.

8. The endoscope system according to claim 1, wherein said overall length of said flexible tube is between 30 to 70 cm.

9. The endoscope system according to claim 1, wherein said flexible tube communicates with any one of a group consisting of and aeration channel, a perfusion channel, an aeration tube and a perfusion tube.

10. An endoscope system, comprising:

an endoscope having an insertional part, an operation unit, and a connector unit wherein said connector unit is connected to said operation unit via a universal chord including tubes and said insertional part is connected to said operation unit via channels, said insertional part having a distal section, wherein said distal section has an opening formed therein for communicating with said operation unit via said channels; and at least one cleaning means for cleaning out any one of a group consisting of said tubes between said connector unit and said operation unit and said channels between said insertional part and said operation unit, said cleaning means having a flexible tube that can be connected to an opening formed in any one of a group consisting of said operation unit said connector unit of said endoscope;

said cleaning means having a tank with a content volume larger than a combined content volume of said flexible tube of said cleaning means and any one of a group consisting of said tubes connecting said connector unit to said operation unit and said channels connecting said insertional part to said connector unit to which said flexible tube is connected to for communicating therewith via said opening.

11. The endoscope system according to claim 10, wherein said cleaning means is a syringe such that a tapered section of a distal portion of said syringe and at least one end of said flexible tube can be connected to each other watertightly.

12. The endoscope system according to claim 11, wherein said flexible tube communicates with at least one of a group consisting of an aeration channel, a perfusion channel, an aeration tube and a perfusion tube.

13. The endoscope system according to claim 11, wherein said syringe has a capacity ranging from 30 to 50 ml.

14. The endoscope system according to claim 10, wherein at least one end of said flexible tube is provided with a weight.

15. The endoscope system according to claim 14, wherein said flexible tube communicates with at least one of a group consisting of an aeration channel, a perfusion channel, an aeration tube or a perfusion tube.

16. The endoscope system according to claim 10, wherein an overall length of said flexible tube is between 30 to 70 cm.

17. The endoscope system according to claim 10, wherein said flexible tube communicates with at least one to a group of consisting of an aeration channel, a perfusion channel, an aeration tube and a perfusion tube.

18. An endoscope system, comprising:

an endoscope having an insertional part, an operation unit, and a connector unit wherein said connector unit is connected to said operation unit via a universal chord including at least two tubes, and said insertional part is connected to said operation unit via at least two channels, said insertional part having a distal section, wherein said distil section has an opening formed therein for communicating with said operation unit via said channels; and a cleaning means for cleaning out either one of said group consisting of said tubes between said connector unit and said operation unit and said channels between said insertional part and said operation unit, said cleaning means having two flexible tubes, wherein each of said two flexible tube has a first end and a second end such that said first end of each of said two flexible tubes can be watertightly connected to a first opening and second opening formed in said connector unit of said endoscope, respectively;

each of said two flexible tubes having an overall length ranging from between 30 cm to 70 cm, and said first end and each of said two flexible tubes having a same shape.

19. The endoscope system according to claim 18, wherein said first end of each of said two flexible tubes are located closely to and coupled with each other.

* * * * *